(12) United States Patent
Hoon et al.

(10) Patent No.: US 11,324,725 B2
(45) Date of Patent: May 10, 2022

(54) COMPOSITIONS AND METHODS FOR THE INHIBITION OF PRURITUS

(71) Applicant: The United States of America, as represented by the Secretary, Department of Health and Human Services, Bethesda, MD (US)

(72) Inventors: Mark A. Hoon, Kensington, MD (US); Hans Juergen Solinski, Pr. Oldendorf (DE); James Inglese, Bethesda, MD (US); Patricia Dranchak, Gaithersburg, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 43 days.

(21) Appl. No.: 16/761,047

(22) PCT Filed: Nov. 2, 2018

(86) PCT No.: PCT/US2018/058887
§ 371 (c)(1),
(2) Date: May 1, 2020

(87) PCT Pub. No.: WO2019/090039
PCT Pub. Date: May 9, 2019

(65) Prior Publication Data
US 2021/0145800 A1     May 20, 2021

Related U.S. Application Data

(63) Continuation-in-part of application No. 15/979,105, filed on May 14, 2018, now abandoned.
(Continued)

(51) Int. Cl.
*A61K 31/422*    (2006.01)
*A61P 17/04*     (2006.01)
(Continued)

(52) U.S. Cl.
CPC .......... *A61K 31/422* (2013.01); *A61K 31/395* (2013.01); *A61K 31/4439* (2013.01);
(Continued)

(58) Field of Classification Search
CPC ............................ A61K 31/422; A61P 17/04
See application file for complete search history.

(56) References Cited

U.S. PATENT DOCUMENTS

| 5,449,752 A | 9/1995 | Fujii et al. |
| 2009/0181896 A1 | 7/2009 | Sharif et al. |

(Continued)

FOREIGN PATENT DOCUMENTS

WO    WO 2015/085055 A2    6/2015

OTHER PUBLICATIONS

STN Registry file (Sep. 18, 2012) (Year: 2012).*
(Continued)

*Primary Examiner* — Craig D Ricci
*Assistant Examiner* — Janet L Coppins
(74) *Attorney, Agent, or Firm* — Leydig, Voit & Mayer, Ltd.

(57) ABSTRACT

Pharmaceutical compositions comprising a molecular inhibitor of Npr1 are disclosed. Also disclosed are methods of treating, reducing, or preventing acute and/or chronic pruritus in a mammal comprising administering a pharmaceutical composition comprising a molecular inhibitor of Npr1.

2 Claims, 35 Drawing Sheets

Related U.S. Application Data

(60) Provisional application No. 62/581,420, filed on Nov. 3, 2017, provisional application No. 62/667,843, filed on May 7, 2018.

(51) Int. Cl.

| | |
|---|---|
| *A61K 31/5513* | (2006.01) |
| *A61K 31/55* | (2006.01) |
| *A61K 31/506* | (2006.01) |
| *A61K 31/4439* | (2006.01) |
| *A61K 31/497* | (2006.01) |
| *A61K 31/395* | (2006.01) |
| *A61K 31/4545* | (2006.01) |

(52) U.S. Cl.
CPC ........ *A61K 31/4545* (2013.01); *A61K 31/497* (2013.01); *A61K 31/506* (2013.01); *A61K 31/55* (2013.01); *A61K 31/5513* (2013.01); *A61P 17/04* (2018.01)

(56) References Cited

U.S. PATENT DOCUMENTS

| | | |
|---|---|---|
| 2015/0320827 A1 | 11/2015 | Carstens et al. |
| 2017/0014486 A1 | 1/2017 | Hoon et al. |

OTHER PUBLICATIONS

STN Registry listing for Compound No. 1394592-04-1, Chembridge Corp 2012 (Year: 2012).*
Aagaard et al. "A Facile Lentiviral Vector System for Expression of Doxycycline-Inducible shRNAs: Knockdown of the Pre-miRNA Processing Enzyme Drosha," *Mol. Ther.*, 15 (5): 938-945 (2007).
Adler et al., "A Novel Family of Mammalian Taste Receptors," *Cell*, 100: 693-702 (2000).
Akiyama et al., "Neural Processing of Itch," *Neuroscience*, 250: 697-714 (2013).
American Chemical Society, STN Registry No. 1394592-04-1 (Sep. 18, 2012).
Austin et al., "NIH Molecular Libraries Initiative," *Science*, 306: 1138-1139 (2004).
Avdeef et al., "Drug absorption in vitro model: filter-immobilized artificial membranes. 2. Studies of the permeability properties of lactones in Piper methysticum Forst," *Eur. J. Pharm. Sci.*, 14: 271-280 (2001).
Caterina et al., "Impaired Nociception and Pain Sensation in Mice Lacking the Capsaicin Receptor," *Science*, 288: 306-313 (2000).
Cavanaugh et al., "Distinct subsets of unmyelinated primary sensory fibers mediate behavioral responses to noxious thermal and mechanical stimuli," *PNAS*, 106(22): 9075-9080 (2009).
Fleming et al., "The majority of dorsal spinal cord gastrin releasing peptide is synthesized locally whereas neuromedin B is highly expressed in pain- and itch-sensing somatosensory neurons," *Mol. Pain*, 8: 52 (2012).
Gong et al., "A gene expression atlas of the central nervous system based on bacterial artificial chromosomes," *Nature*, 425: 917-925 (2003).
Han et al., "Phospholipase Cβ 3 Mediates the Scratching Response Activated by the Histamine H1 Receptor on C-Fiber Nociceptive Neurons," *Neuron*, 52: 691-703 (2006).
Han et al., "A subpopulation of nociceptors specifically linked to itch," *Nat. Neurosci.*, 16(2): 174-182 (2012).
Hirata et al., "Role of Endogenous Atrial Natriuretic Peptide in DOCA-Salt Hypertensive Rats: Effects of a Novel Nonpeptide Antagonist for Atrial Natriuretic Peptide Receptor," *Circulation*, 87: 554-561 (1993).
Hoon et al., "Putative Mammalian Taste Receptors: A Class of Taste-Specific GPCRs with Distinct Topographic Selectivity," *Cell*, 96: 541-551 (1999).
Hoon et al., "Molecular dissection of itch," *Curr. Opin. Neurobiol.*, 34: 61-66 (2015).
Hudecz, F., "Synthesis of Peptide Bioconjugates," *Methods Mol. Biol.*, 298: 209-223 (2005).
Imamachi et al., "TRPV1-expressing primary afferents generate behavioral responses to pruritogens via multiple mechanisms," *PNAS*, 106(27): 11330-11335 (2009).
Inglese et al., "Quantitative high-throughput screening: A titration-based approach that efficiently identifies biological activities in large chemical libraries," *PNAS*, 103(31): 11473-11478 (2006).
European Patent Office, International Search Report for International Patent Application No. PCT/US2014/068541 (dated Jun. 17, 2015).
European Patent Office, International Search Report for International Patent Application No. PCT/US2018/058887 (dated Apr. 16, 2019).
European Patent Office, Written Opinion of the International Searching Authority for International Patent Application No. PCT/US2014/068541 (dated Jun. 16, 2015).
European Patent Office, Written Opinion of the International Searching Authority for International Patent Application No. PCT/US2018/058887 (dated Apr. 16, 2019).
International Bureau of WIPO, International Preliminary Report on Patentability for International Patent Application No. PCT/US2014/068541 (dated Jun. 7, 2016).
Ito et al., "A Medium-Term Rat Liver Bioassay for Rapid In Vivo Detection of Carcinogenic Potential of Chemicals," *Cancer Sci.* 94(1):3-8 (Jan. 2003).
Jang et al., "Identification of Drug Modulators Targeting Gene-Dosage Disease CMT1A," *ACS Chem. Bio.*, 7:1205-1213 (2012).
Kirin et al., "Amino Acid and Peptide Bioconjugates of Copper(II) and Zinc(II) Complexes with a Modified N,N-Bis(2-picolyl)amine Ligand," *Inorg. Chem.*, 44(15): 5405-5415 (2005).
Liu et al., "Sensory Neuron-Specific GPCR Mrgprs Are Itch Receptors Mediating Chloroquine-Induced Pruritus," *Cell*, 139: 1353-1365 (2009).
Liu et al., "The Distinct Roles of Two GPCRs, MrgprC11 and PAR2, in Itch and Hyperalgesia," *Sci. Signal.*, 4(181): ra45 (2011).
Malo et al., "Statistical practice in high-throughput screening data analysis," *Nat. Biotechnol.*, 24(2): 167-175 (2006).
McNeil et al., "Peripheral mechanisms of itch," *Neuroscience Bulletin*, 28(2): 100-110 (2012).
Mishra et al., "A principle neurotransmitter Nppb and its role in itch sensation," 43rd Annual Meeting of the Society for Neuroscience, San Diego, CA, Presentation Abstract Poster 831.20/KK7 (Nov. 13, 2013).
Mishra et al., "The Cells and Circuitry for Itch Responses in Mice," *Science*, 340(6135): 968-971 and Supplementary Material (2013).
Mishra et al., "A Nociceptive Signaling Role for Neuromedin B," *J. Neurosci.*, 32 (25): 8686-8695 (2012).
Mishra et al., "TRPV1-lineage neurons are required for thermal sensation," *EMBO J.*, 30: 582-593 (2011).
Misono et al., "Structure, signaling mechanism and regulation of the natriuretic peptide receptor guanylate cyclase," *The FEBS Journal*, 278: 1818-1829 (2011).
Miyoshi et al., "Effect of Natriuretic Peptide Receptor Antagonist on Lipopolysaccharide-Induced Fever in Rats: Is Natriuretic Peptide an Endogenous Antipyretic?" *J. Pharmacol. Exp. Ther.*, 318(3): 1163-1170 (2006).
Ohyama et al., "HS-142-1, A novel Antagonist for Natriuretic Peptides, Has No Effect on the Third Member of Membrane bound Guanylate Cyclases (GC-C) in T84 Cells," *Life Sciences*, 52: PL153-PL157 (1993).
Park, et al., "Diethylnitrosamine (DEN) induces irreversible hepatocellular carcinogenesis through overexpression of G1/S-phase regulatory proteins in rat," *Toxicol Lett.*, 191(2-3): 321-6 (2009).
Poirier et al., "Allotopic antagonism of the non-peptide atrial natriuretic peptide (ANP) antagonist HS-142-1 on natriuretic peptide receptor NPR-A," *Biochem. J.*, 362: 231-237 (2002).
National Institutes of Health, Press Release entitled "NIH Scientists Discover Molecule Triggers Sensation of Itch" [www.nih.gov/news/health/may2013/nidcr-23.htm] (May 23, 2013).

(56) References Cited

OTHER PUBLICATIONS

Raap et al., "Pathophysiology of itch and new treatments," *Curr. Opin. in Allergy and Clin. Immuno.*, 11(5): 420-427 (2011).
Sano et al., "Pharmacological Profile of HS-142-1, A Novel Nonpeptide Atrial Natriuretic Peptide Antagonist of Microbial Origin. I. Selective Inhibition of the Actions of Natriuretic Peptides in Anesthetized Rats," *J. Pharmacol. Experiment. Therap.*, 260(2): 825-831 (1992).
Shim et al., "TRPV1 Mediates Histamine-Induced Itching via the Activation of Phospholipase A2 and 12-Lipoxygenase," *J. Neurosci.*, 27(9): 2331-2337 (2007).
Solinski et al., "Development of a screening platform for natriuretic peptide receptor 1 antagonists," poster presented at the annual meeting of the Society for Neuroscience in Chicago (Oct. 20, 2015).
Sun et al., "A gastrin-releasing peptide receptor mediates the itch sensation in the spinal cord," *Nature*, 448: 700-704 (2007).
Sun et al., "Cellular Basis of Itch Sensation," *Science*, 325(5947): 1531-1534 (2009).
Toki et al., "HS-142-1, a novel non-peptide ANP antagonist, blocks the cyclic GMP production elicited by natriuretic peptides in PC12 and NG108-15 cells," *Neurosci. Letters*, 135: 117-120 (1992).
Vilotti et al., "B-Type Natriuretic Peptide-Induced Delayed Modulation of TRPV1 and P2X3 Receptors of Mouse Trigeminal Sensory Neurons," *PLOS ONE*, 8(11): e81138 (2013).
Wiley et al., "Targeted toxins in pain," *Advanced Drug Delivery Reviews*, 55: 1043-1054 (2003).
Yegen et al., "Inhibitory effects of gastrin releasing peptide on gastric emptying in rats," *Regulatory Peptides*, 61: 175-180 (1996).
Zhang et al., "HS-142-1, A Potent Antagonist of Natriuretic Peptides In Vitro and In Vivo," *J. Am. Soc. Nephrol.*, 5: 1099-1105 (1994).
U.S. Appl. No. 15/979,105, filed May 14, 2018.

\* cited by examiner

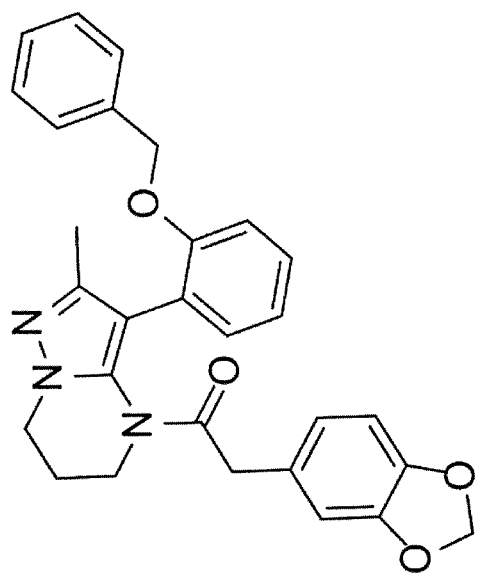
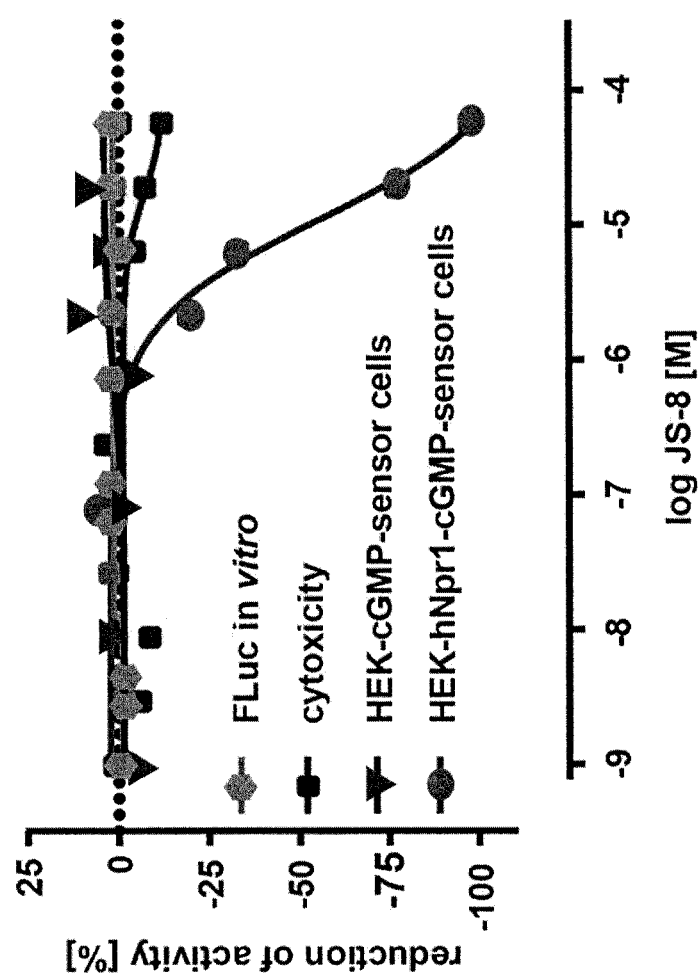
Figure 3C
Figure 3D

COMPOSITIONS AND METHODS FOR THE INHIBITION OF PRURITUS

CROSS-REFERENCE TO RELATED APPLICATIONS

This patent application is the U.S. national phase of PCT/US2018/058887, filed Nov. 2, 2018, which claims the benefit of U.S. Provisional Patent Application No. 62/581,420, filed Nov. 3, 2017, U.S. Provisional Patent Application No. 62/667,843, filed May 7, 2018, and U.S. patent application Ser. No. 15/979,105, filed May 14, 2018, all of which are incorporated by reference in their entireties.

STATEMENT REGARDING FEDERALLY SPONSORED RESEARCH AND DEVELOPMENT

This invention was made with Government support under project number DE000721 by the National Institutes of Health, National Institute of Dental and Craniofacial Research. The Government has certain rights in the invention.

BACKGROUND OF THE INVENTION

Pruritus (alternatively spelled, "pruritis"), or itch, is an irritating skin sensation that provokes a desire to scratch. Pruritus may range from mildly unpleasant and temporary to acute and persistent sensations. A number of skin (e.g., fungal infections, and skin conditions such as atopic dermatitis) and systemic conditions (e.g., renal failure, liver damage, liver disease (e.g., cirrhosis), acquired immune deficiency syndrome (AIDS), polycythemia vera, diabetes, hyperthyroidism, and cancer (e.g., Hodgkin's lymphoma, non-Hodgkin's lymphoma, and Kaposi's sarcoma) may be associated with acute and/or chronic pruritus, which can significantly reduce quality of life. Other causes of pruritus may include induction by cytokines or treatments such as chemotherapy and kidney dialysis.

Conventional treatments of pruritus include prescription and over-the-counter medications, including topical anti-inflammatory agents, anti-histamines, and emollients, which are aimed at managing the itchy sensation. However, without eradication of the underlying disease, treatment of pruritus often is ineffective and may be frustrating for patients and prescribing physicians. Thus, the treatment of pruritus continues to be a diagnostic and therapeutic challenge, such that there is a need for improved compositions and methods for treating pruritus.

BRIEF SUMMARY OF THE INVENTION

An embodiment of the invention provides a pharmaceutical composition comprising a pharmaceutically acceptable carrier and a molecular inhibitor of Natriuretic polypeptide receptor 1 ("Npr1,"), which is a receptor for, inter alia, neuropeptide natriuretic polypeptide B ("Nppb" or "NppB"). Details concerning Npr1 and NppB are discussed in U.S. patent application Ser. No. 15/039,982 (U.S. Patent Application Publication No. 2017-0014486 A1), which is incorporated herein in its entirety by reference.

Another embodiment of the invention provides a method of treating, reducing, or preventing acute and/or chronic pruritus in a mammal comprising administering a pharmaceutical composition comprising a pharmaceutically acceptable carrier and a molecular inhibitor of Npr1, thereby treating, reducing, or preventing acute and/or chronic pruritus in the mammal.

Another embodiment of the invention provides a pharmaceutical composition comprising (a) a pharmaceutically acceptable carrier and (b) a molecular inhibitor of Natriuretic polypeptide receptor 1 ("Npr1"), wherein the molecular inhibitor of Npr1 is 1-cyclohexyl-3-(cyclopropylmethyl)-N-((3-methylisoxazol-5-yl)methyl)-2-oxo-2,3-dihydro-1H-benzo[d]imidazole-5-carboxamide.

Another embodiment of the invention provides a method of treating, reducing, or preventing acute and/or chronic pruritus in a mammal comprising administering a pharmaceutical composition comprising (a) a pharmaceutically acceptable carrier and (b) a molecular inhibitor of Npr1, thereby treating, reducing, or preventing acute and/or chronic pruritus in the mammal, wherein the molecular inhibitor of Npr1 is 1-cyclohexyl-3-(cyclopropylmethyl)-N-((3-methylisoxazol-5-yl)methyl)-2-oxo-2,3-dihydro-1H-benzo[d]imidazole-5-carboxamide.

Further embodiments of the invention provide methods of treating, reducing, or preventing acute and/or chronic pruritus in a mammal wherein the acute and/or chronic pruritus is associated with a skin condition, a systemic condition, induced by a pruritogen, or induced by a cytokine. Additional embodiments of the invention provide methods of treating, reducing, or preventing acute and/or chronic pruritus in a mammal wherein the pruritus is associated with kidney dialysis or chemotherapy.

BRIEF DESCRIPTION OF THE SEVERAL VIEWS OF THE DRAWING(S)

FIG. 1A is a schematic depicting the signaling pathway employed in the cell-based assay for assessing Npr1 receptor activity. Npr1 is stimulated by Nppa or Nppb peptides, which elicit activation of cyclase and production of cGMP. In turn, cGMP levels can be measured by cGMP binding to the PDE5 moiety of the cGMP sensor (pGS-40F) through which a conformational change activates Firefly luciferase domains producing light.

FIG. 1B is a graph showing concentration response curves for HEK293 cells transiently expressing mNpr1 and pGS-40F stimulated by a concentration titration of natriuretic peptides mNppa, mNppb, and Nppc. Increases of light emission in cells stimulated with natriuretic peptides showed that mNpr1 is potently activated by Nppb and Nppa, but is only activated by high concentrations of Nppc. Data represent means±SEM of duplicate measurements.

FIG. 1C is a graph showing HEK293 cells transiently expressing mNpr1 and pGS-40F treated with A-71915. Five minutes after addition of A-71915, cells were treated with 1 nM mNppb. Treatment with mNppb activated cells which is inhibited by A-71915. Data represent means±SEM of duplicate measurements.

FIG. 1D is a is a graph showing HEK293 cells transiently expressing mNpr1 and pGS-40F treated with A-71915. Treatment with A-71915 directly stimulates basal mNpr1 activity showing that it is a partial agonist. Data represent means±SEM of duplicate measurements.

FIG. 1E is a schematic of hNppa and A-71915 showing their similar cyclic structures. Non-proteinogenic amino acids are indicated (Cha, cyclohexylalanine; D-Tic, D-1,2,3,4-tetrahydoisoquinoline-3-carboxylic acid).

FIG. 2A is a graph of a time course experiment showing increases in luciferase activity in stable HEK-hNpr1-cGMP-sensor cells expressing pGS-40F and hNpr1. Natriuretic peptides hNppa and hNppb (10 nM each) elicited increases in luciferase activity. Nppc (10 nM) did not elicit an increase in luciferace activity. Data represent means±SEM of duplicate measurements.

FIG. 2B is a graph showing the titration of natriuretic peptides hNppa, hNppb, and Nppc. This demonstrated that HEK-hNpr1-cGMP-sensor cells exhibit the appropriate stimulation potencies to different peptides; rank order of potency of ligands was hNppa>hNppb>>>Nppc. Data represent means±SEM of duplicate measurements.

FIG. 2C is a graph of a time course experiment showing increases in luciferase activity of stable cells expressing pGS-40F. The HEK-cGMP-sensor cells are stimulated by SNP, but not by natriuretic peptides hNppa, hNppb, and Nppc. Data represent means±SEM of duplicate measurements.

FIG. 2D is a graph showing the response in stable HEK-cGMP-sensor cells expressing pGS-40F to hNppa, SNP, Nppc, and Nppb. The HEK-cGMP-sensor cells are stimulated by SNP, but not by natriuretic peptides hNppa, Nppc, or Nppb. Data represent means±SEM of duplicate measurements.

FIG. 2E is a schematic depicting the protocol time course for the qHTS assay. Reads before and after agonist addition enabled measurement of effects of compounds on both basal and agonist-induced hNpr1 activity.

FIG. 2F is a 3-axis plot for concentration-response curve profiles for compounds from the Genesis chemical library (86,437 compounds). In total, 519,417 concentration response values are displayed (1574 out-lying values were not plotted). The displayed fit curves (black traces) are for 105 compounds with a maximum antagonism of >90% (i.e., greater than 90%). Curves were fit using a four-parameter logistic regression.

FIG. 3C is a graph showing that compound JS-8 inhibits hNppa-induced hNpr1 activity in HEK-hNpr1-cGMP-sensor cells, does not inhibit Firefly luciferase (FLuc in vitro), does not block SNP-induced GloSensor™ signals (in HEK-cGMP-sensor cells), and does not produce cytotoxicity. Data are measurements from the qHTS assays.

FIG. 3D is a schematic diagram of the chemical structure of JS-8.

Figure 4A:
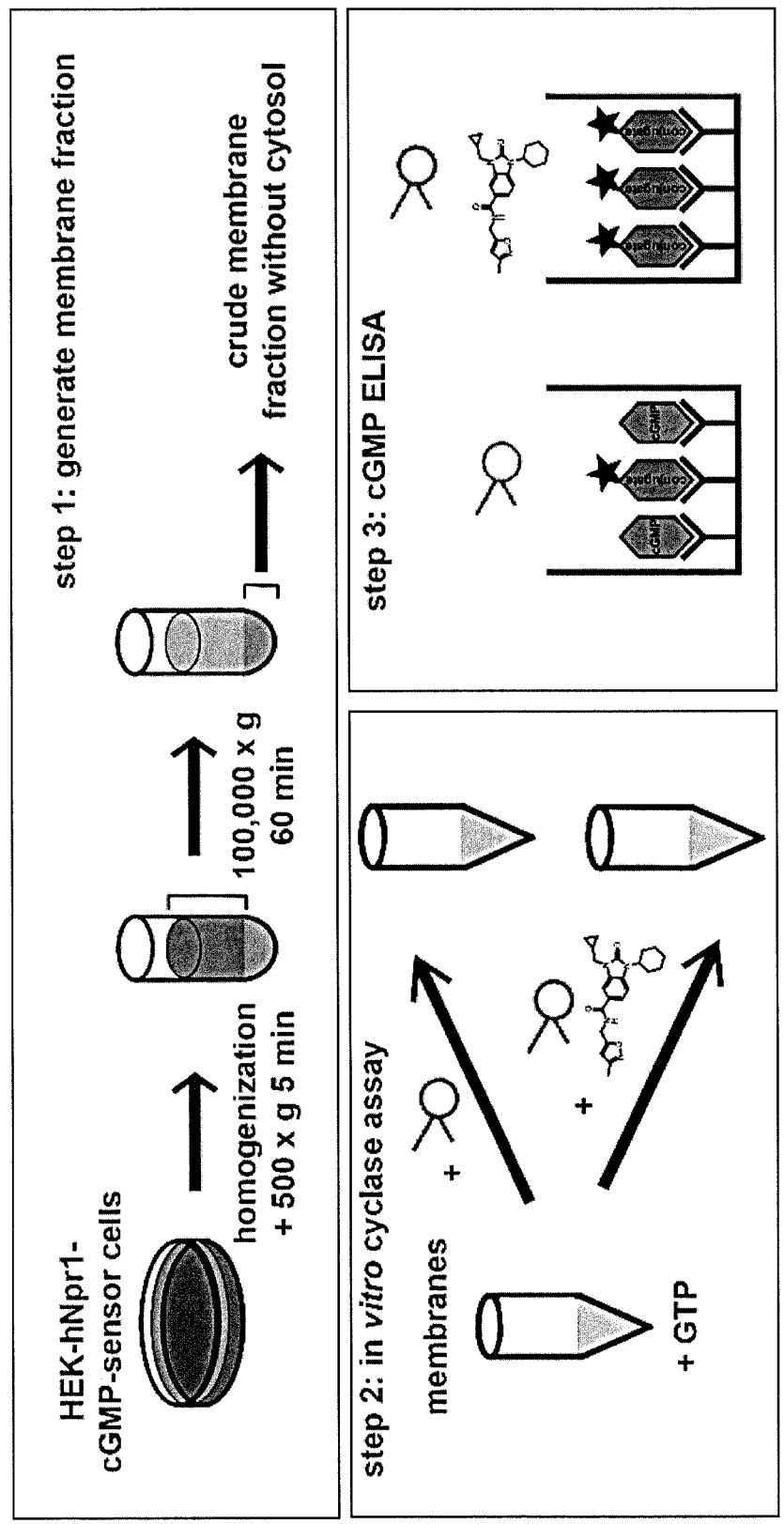

FIG. 4A is a schematic diagram depicting the principle steps of the in vitro membrane cyclase assay. A crude membrane fraction is obtained after mechanical disruption of HEK-hNpr1-cGMP-sensor cells (step 1). Incubation of hNpr1 membranes with GTP (step 2) generates cGMP (measured using ELISA) from the natriuretic peptide stimulated receptor and inhibition of this reaction can be assessed (step 3).

Figure 4B:
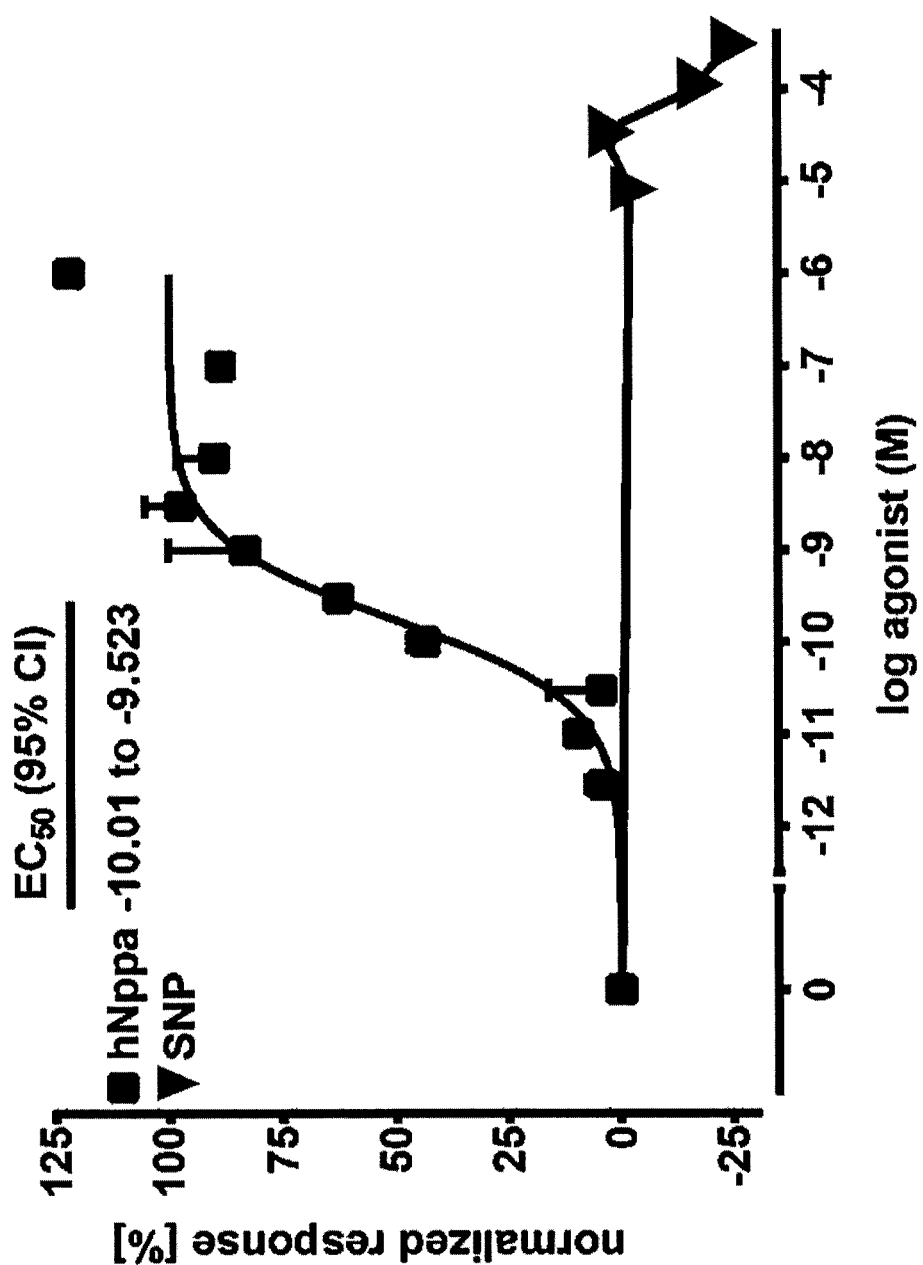

FIG. 4B is a graph showing that dose dependence of hNpr1 membrane production of cGMP to hNppa and SNP is demonstrative of the specificity and sensitivity of the cell-free assay. Data represent means±SEM of triplicate (single measurement for SNP).

Figure 4C:
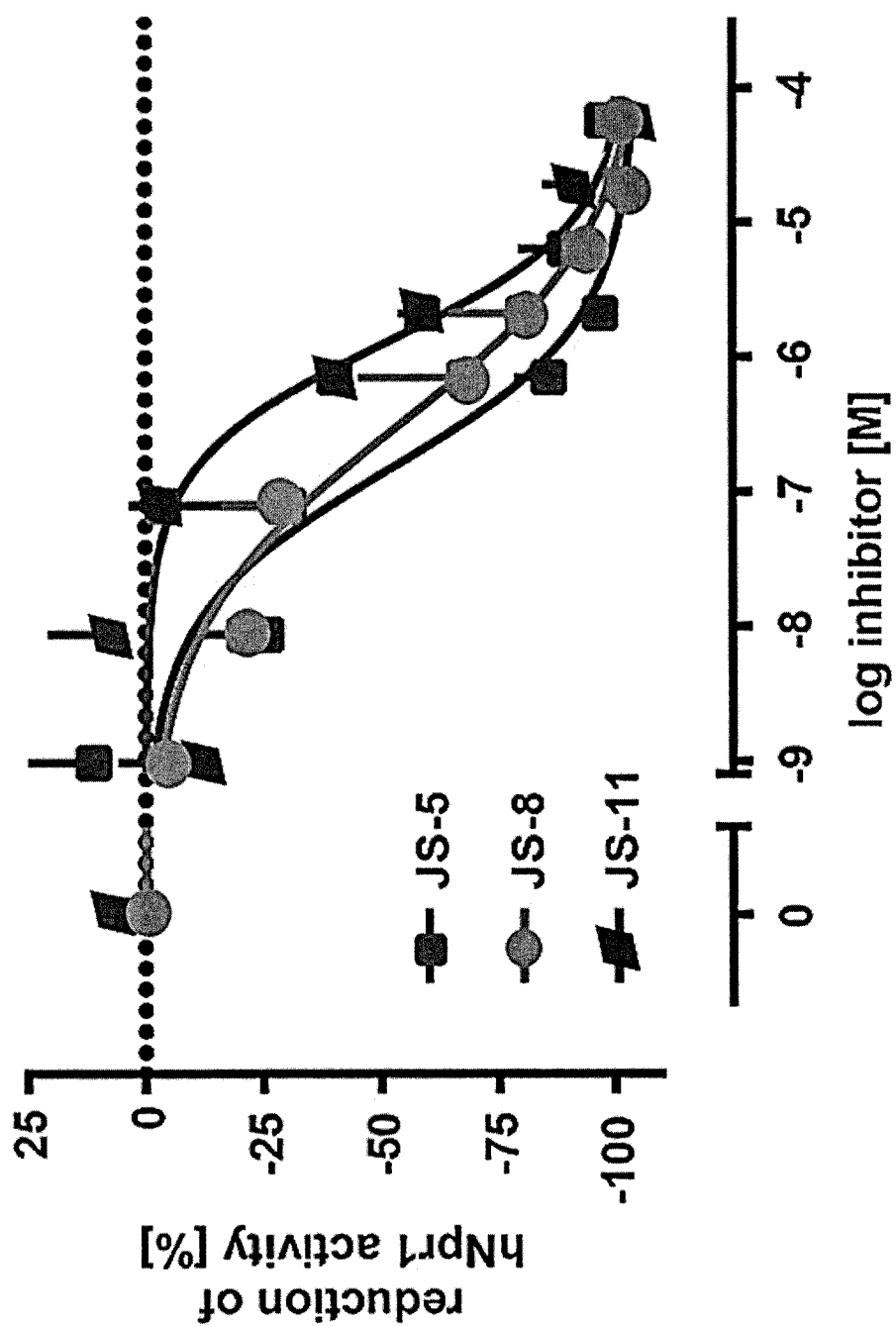

FIG. 4C is a graph showing the inhibition of hNpr1 agonist-induced activity after membranes were incubated with 1 nM hNppa and JS-5, JS-8 or JS-11. Data represent means±SEM of triplicate and duplicate measurements.

Figure 5A:
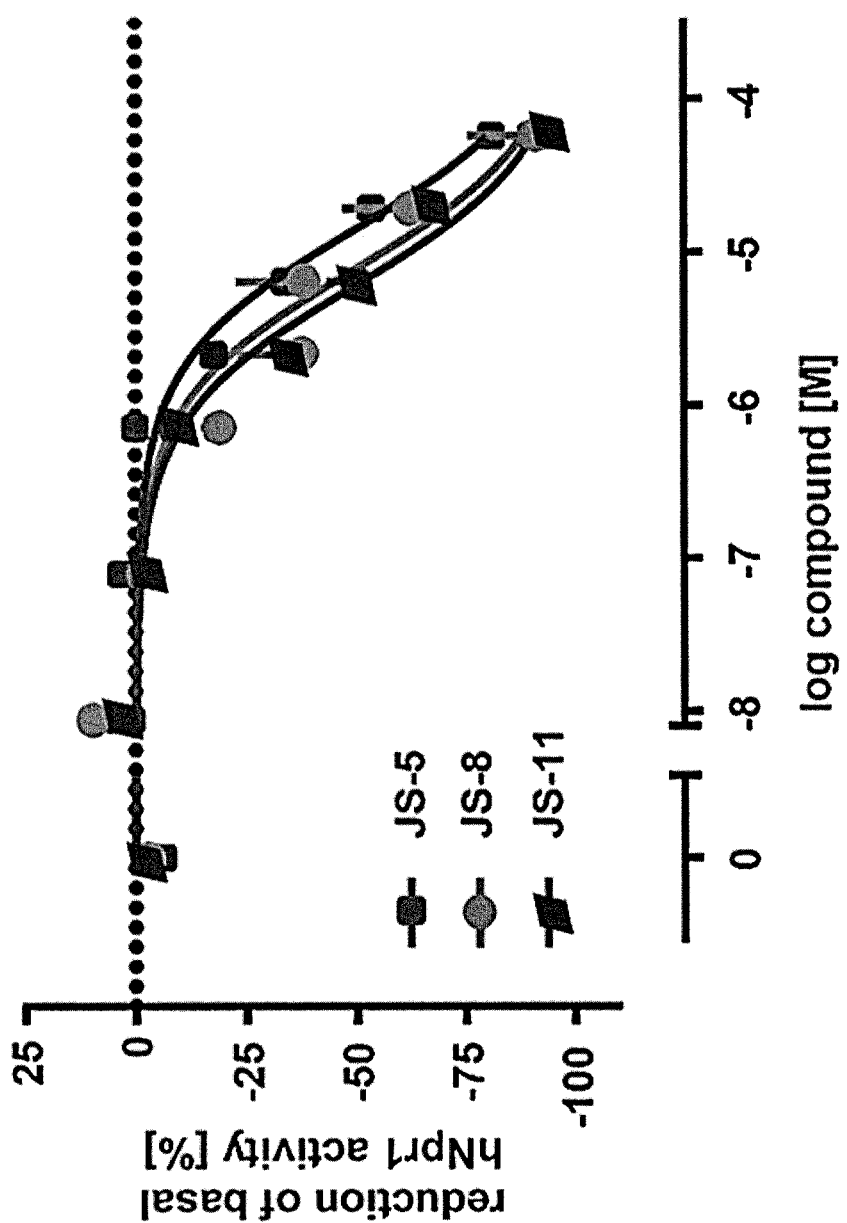

FIG. 5A is a graph showing that basal hNpr1 activity (unstimulated activity) in HEK-hNpr1-cGMP-sensor cells was dose dependently inhibited by hNpr1 antagonists JS-5, JS-8, and JS-11. Data represent means±SEM of triplicate measurements.

Figure 5B:
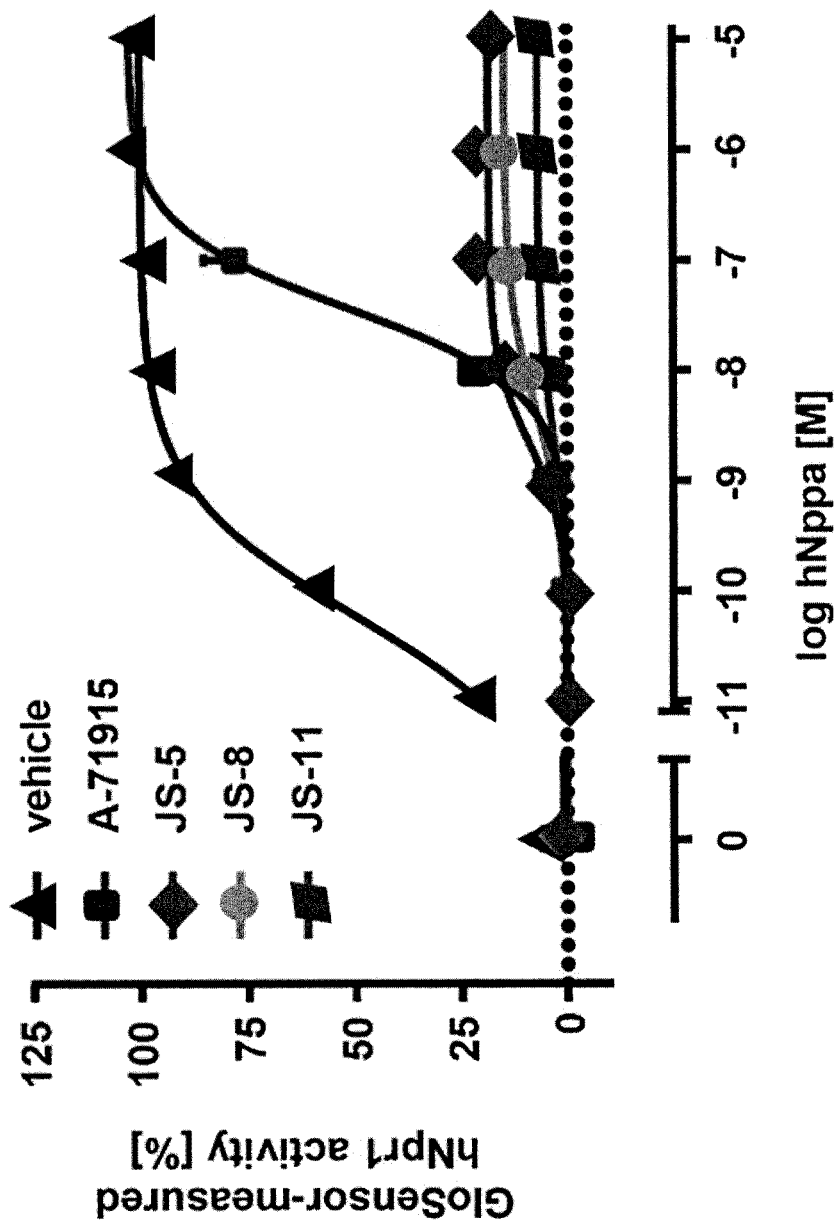

FIG. 5B is a graph showing the measurement of hNpr1 activity in the cell-based GloSensor™ assay, after hNpr1 expressing cells were treated with a fixed concentration of antagonists (5 µM) prior to the addition of increasing concentrations of hNppa. Data represent means±SEM of duplicate measurements.

Figure 5C:
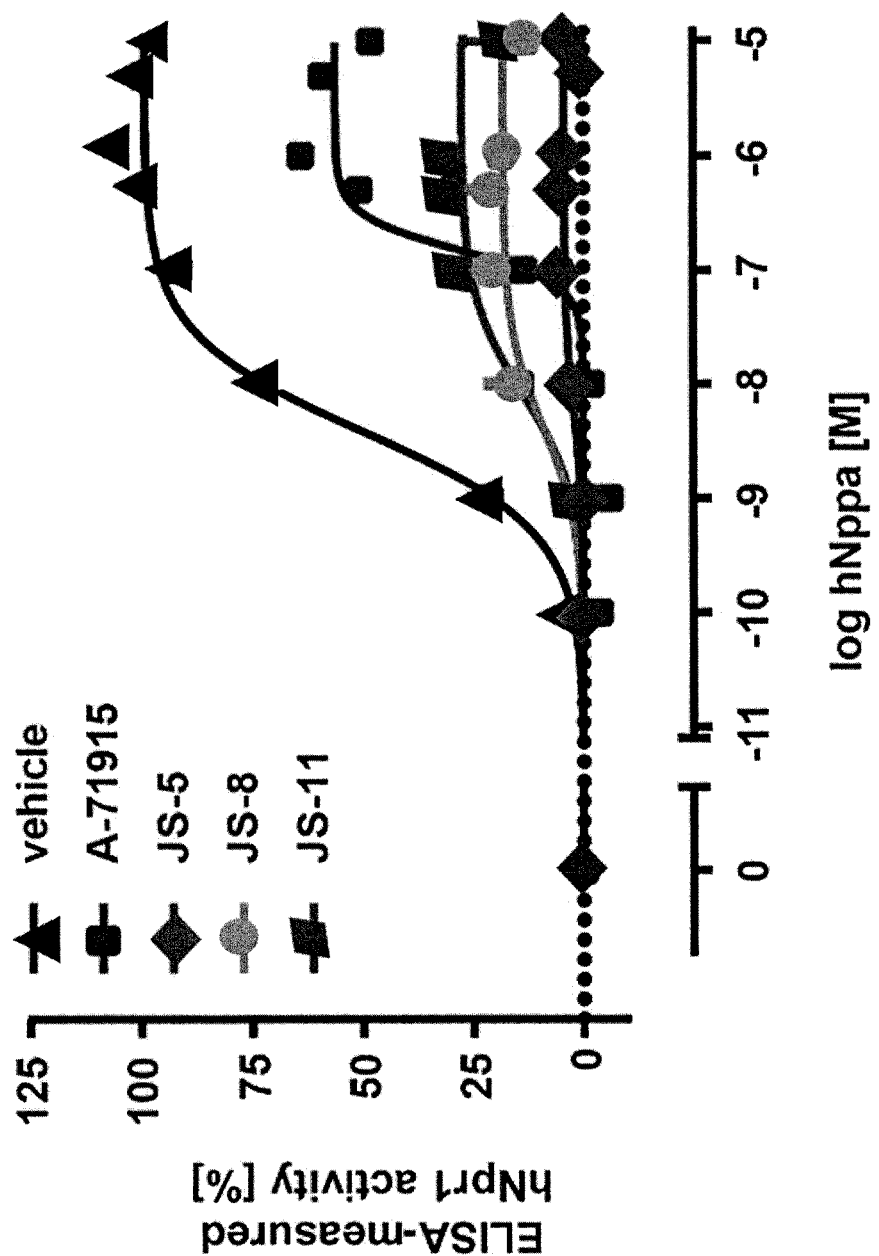

FIG. 5C is a graph showing the measurement of hNpr1 activity in the membrane cyclase assay (ELISA-measured), after hNpr1 expressing membranes were treated with a fixed concentration of antagonists (5 µM) prior to the addition of increasing concentrations of hNppa. Data represent means±SEM of duplicate measurements.

Figure 5D:
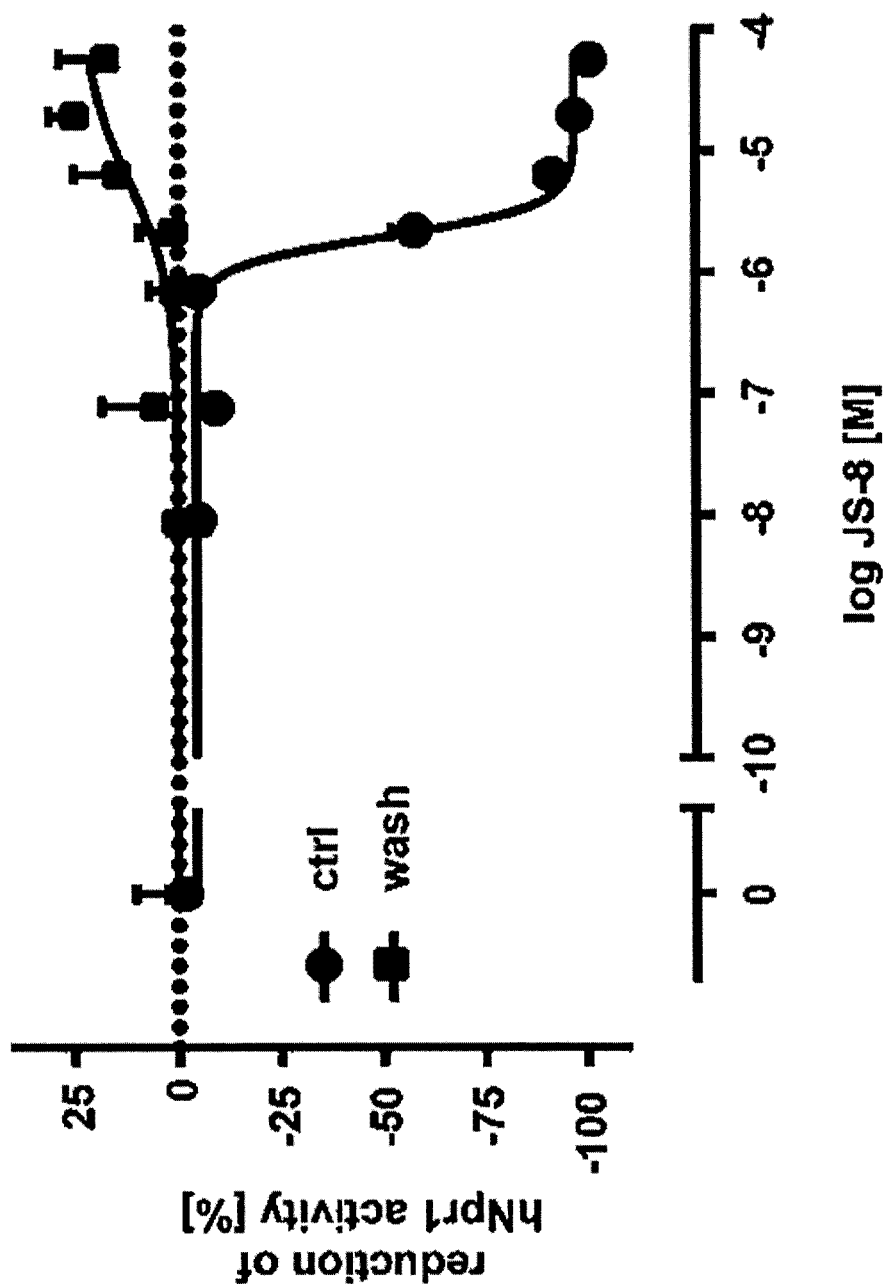

FIG. 5D is a graph showing that the inhibition of hNpr1 by JS-8 is reversible. Compared to the control condition (ctrl; cells acutely pre-treated with JS-8 and immediately stimulated with 60 µM hNppa), washed cells did not exhibit inhibition.

Figure 6A:
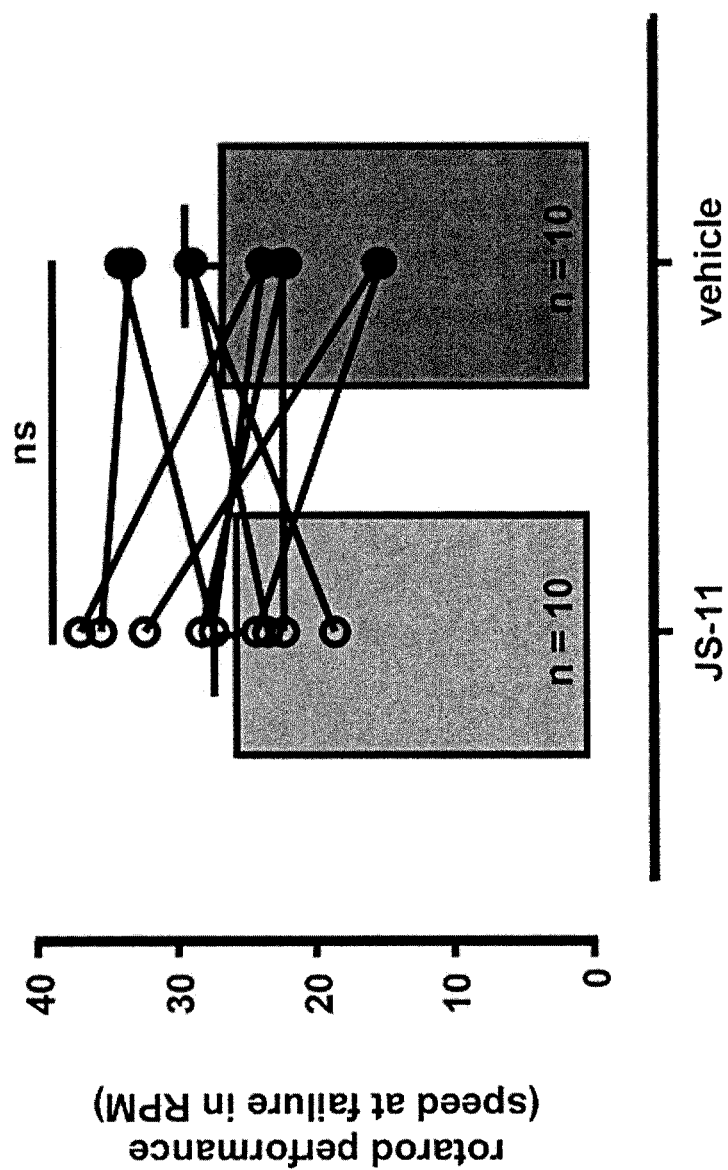

FIG. 6A is a plot of behavioral testing (rotarod performance) initiated 10 minutes after JS-11 treatment. Motor coordination performance, on an accelerating rod, was not significantly altered by JS-11. Data represent means±SEM of n=10 animals.

Figure 6B:
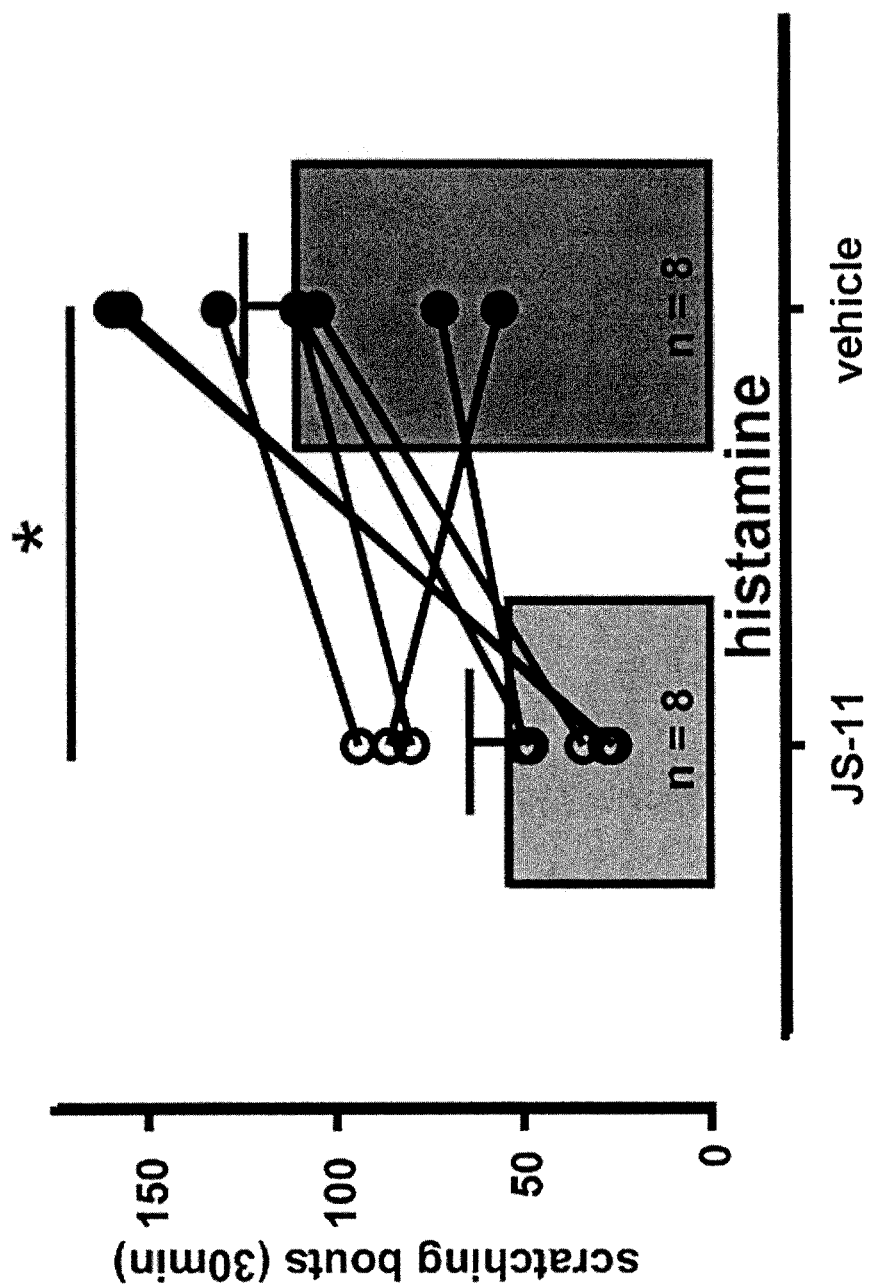

FIG. 6B is a plot of behavioral testing (scratching bouts) initiated 10 minutes after JS-11 treatment. Scratching responses to 100 µg histamine injected intradermally into the nape of the neck were significantly attenuated compared to paired controls by administration of JS-11. Data represent means±SEM of n=8 animals.

Figure 6C:
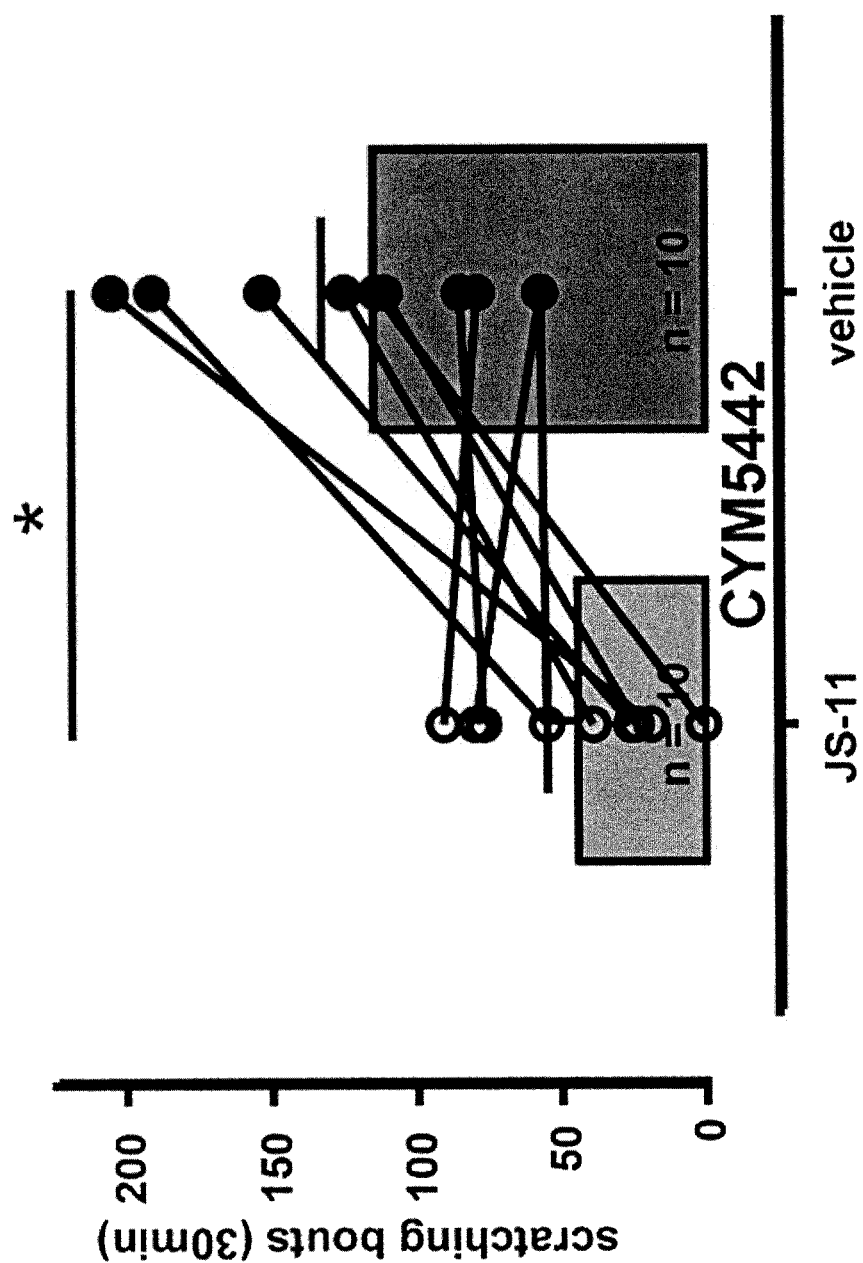

FIG. 6C is a plot of behavioral testing (scratching bouts) initiated 10 minutes after JS-11 treatment. Scratching responses to 8.9 µg CYM5442 injected intradermally into the nape of the neck were significantly attenuated compared to paired controls by administration of JS-11. Data represent means±SEM of n=10 animals.

Figure 6D:
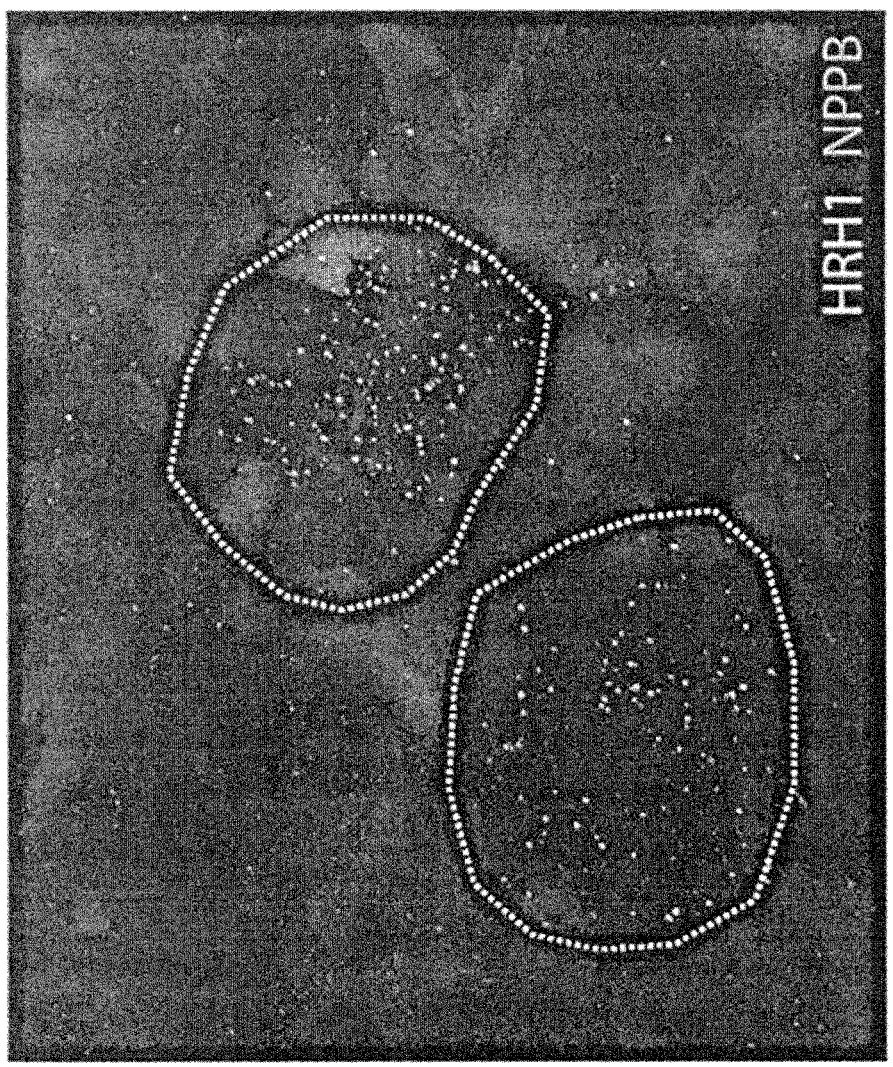

FIG. 6D is a photographic image of double-labelling ISH staining of human DRG sections revealing that NPPB and HRH1 and MRGPRX1 (illuminated dots shown in side of white-doted circles) are co-expressed with each other. The expression of Nppb was determined with development with a green amplified agent and Hrh1 with a red agent. Red and green staining was present in the same neurons. DRG sections were counter-stained with DAPI (grey background). Neurons stained for Nppb and itch-receptors are highlighted within the white-dotted profile circles.

Figure 6E:
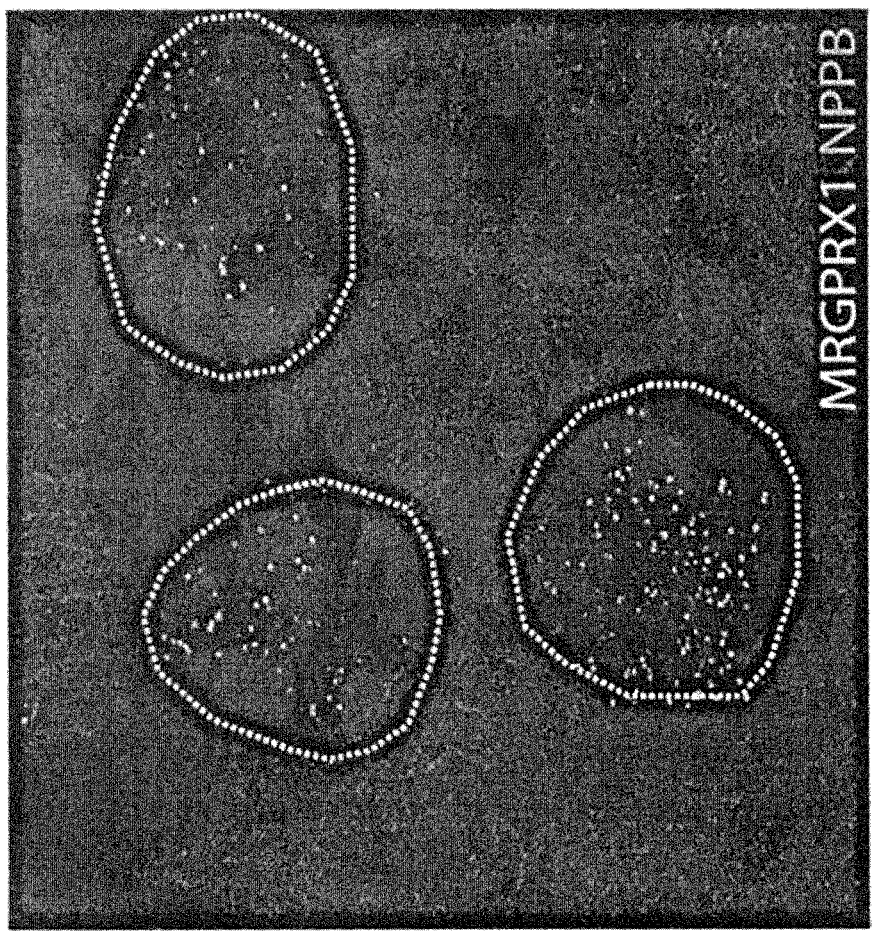

FIG. 6E is a photographic image of double-labelling ISH staining of human DRG sections revealing that Nppb and MRGPRX1 (illuminated dots shown in side of white-doted circles) are co-expressed with each other. The expression of Nppb was determined with development with a green amplified agent and Mrgprx1 with a red agent. Red and green staining was present in the same neurons. DRG sections were counter-stained with DAPI (grey background). Neurons stained for Nppb and itch-receptors are highlighted within the white-dotted profile circles.

Figure 7A:
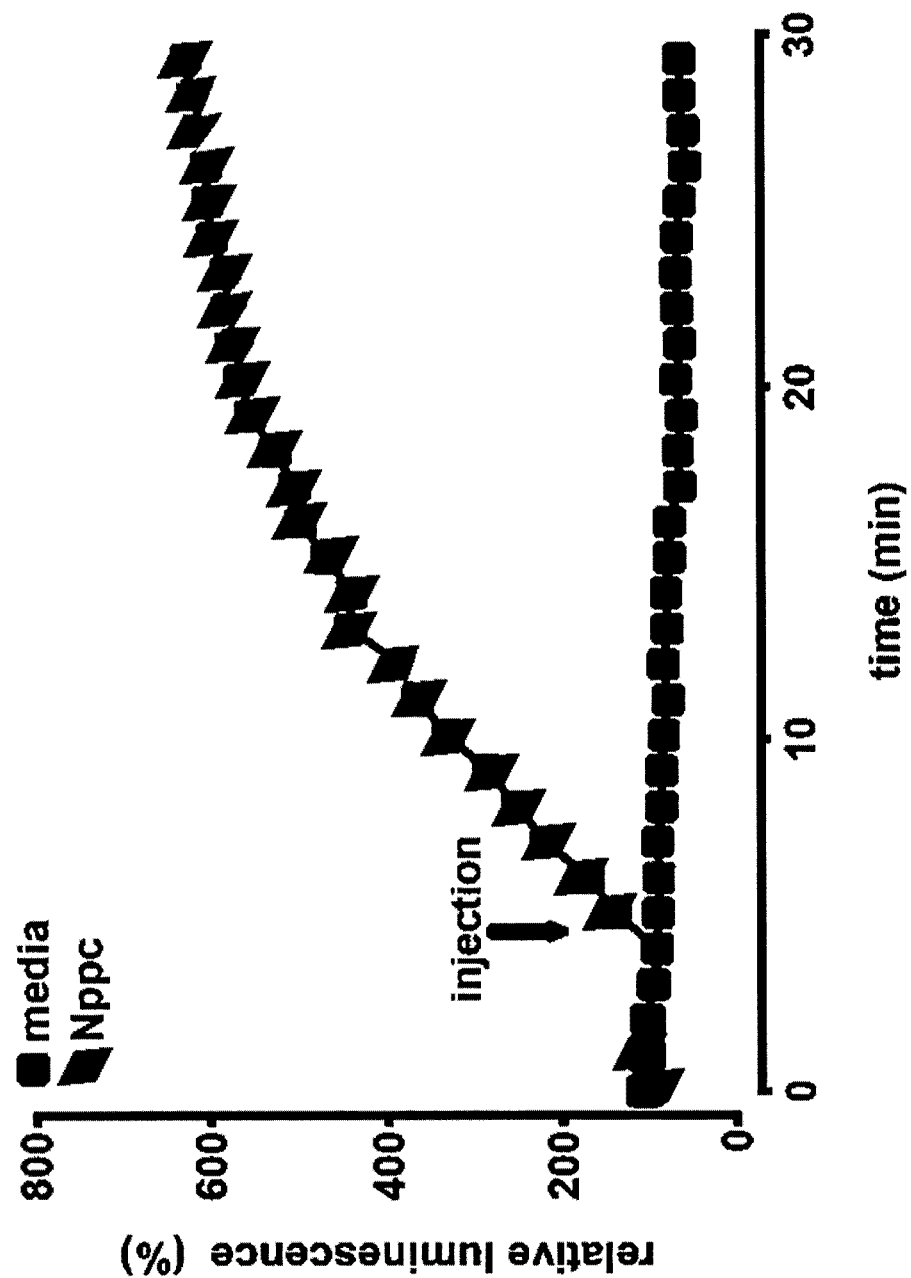

FIG. 7A is a graph of time course experiments showing that 10 nM Nppc elicited an increase in luciferase activity in a cloned cell-line stably expressing pGS-40F with hNpr2 (HEK-hNpr2-cGMP-sensor cells). Data represent means±SEM of duplicate measurements.

Figure 7B:
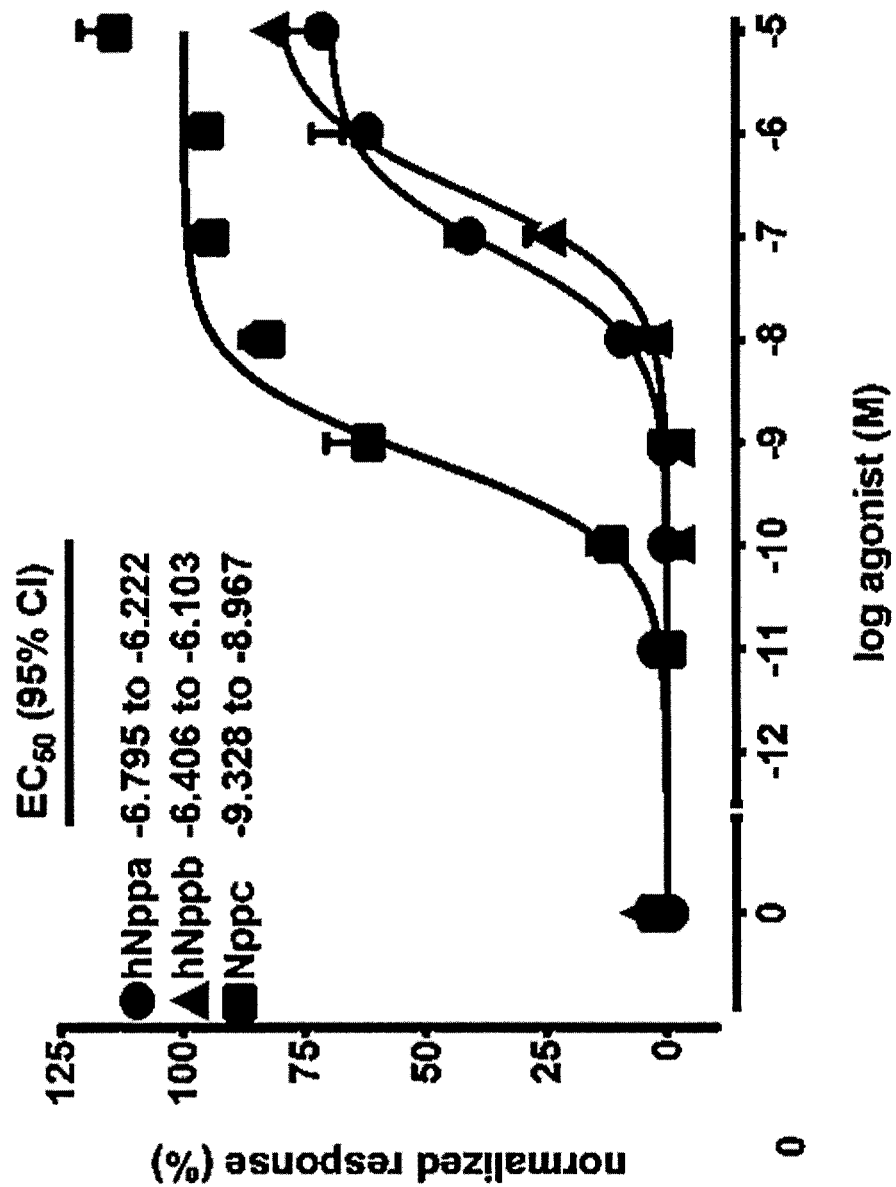

FIG. 7B is a graph showing that titration of natriuretic peptides hNppa, hNppb and Nppc in HEK-hNpr2-cGMP-sensor cells exhibited the appropriate stimulation potencies to different peptides; rank order of potency of ligands was Nppc>>hNppa=hNppb. Data represent means±SEM of duplicate measurements.

Figure 8A:
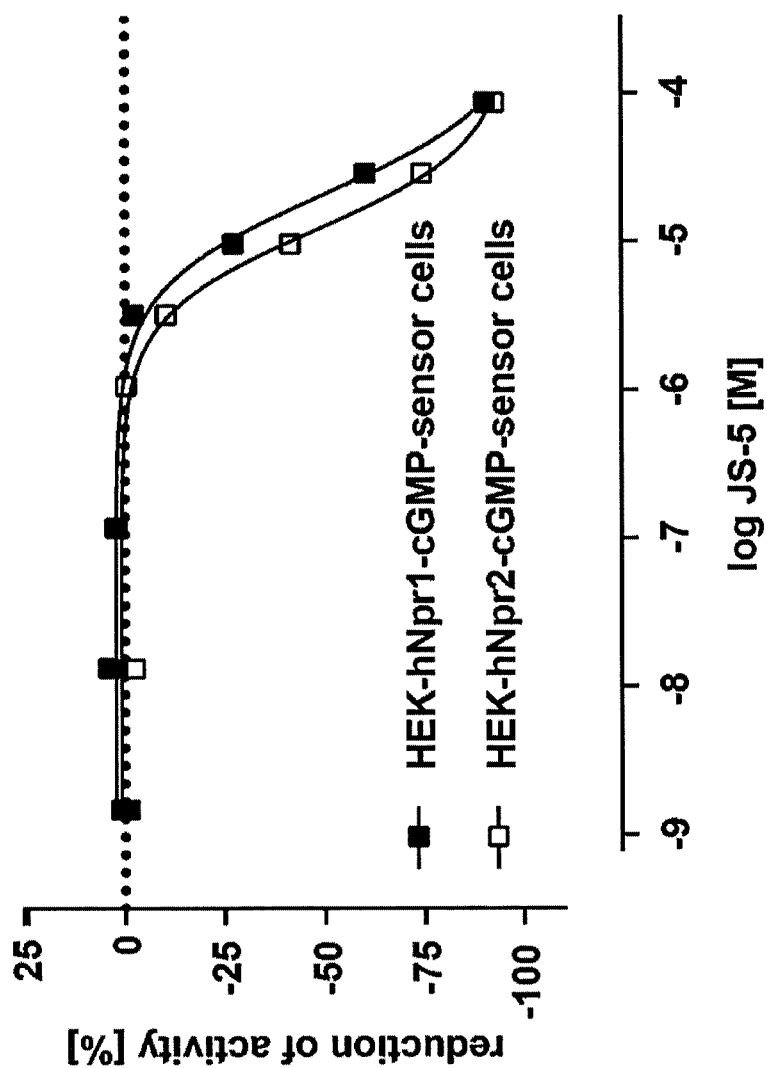

FIG. 8A is a graph showing that titration of JS-5 antagonizes natriuretic peptide-induced activation of HEK-hNpr1-cGMP-sensor cells (with Nppa) and HEK-hNpr2-cGMP-sensor cells (with Nppc).

Figure 8B:
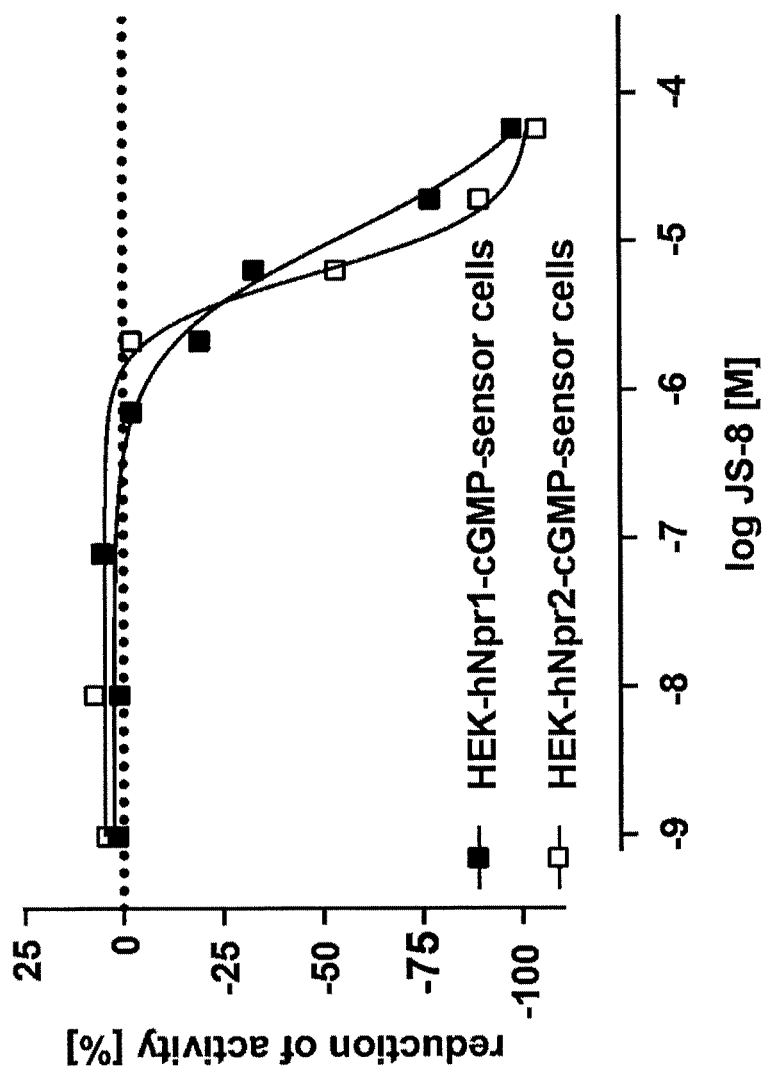

FIG. 8B is a graph showing that titration of JS-8 antagonizes natriuretic peptide-induced activation of HEK-hNpr1-cGMP-sensor cells (with Nppa) and HEK-hNpr2-cGMP-sensor cells (with Nppc).

Figure 8C:
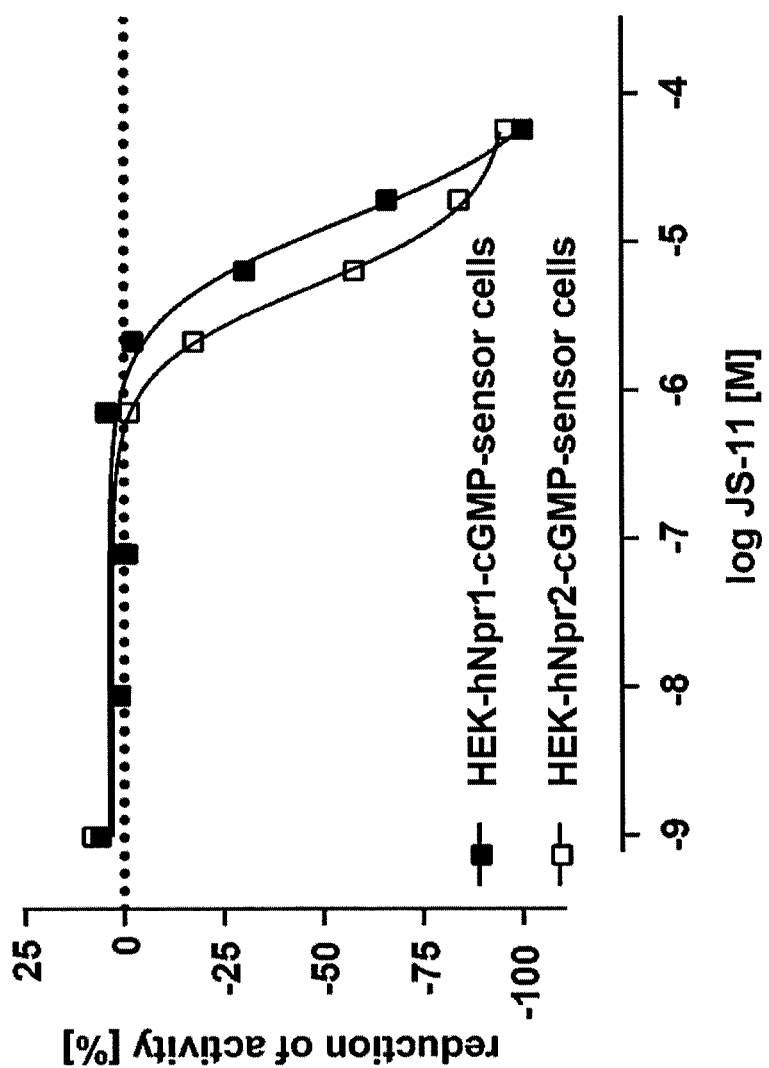

FIG. 8C is a graph showing that titration of JS-11 antagonizes natriuretic peptide-induced activation of HEK-hNpr1-cGMP-sensor cells (with Nppa) and HEK-hNpr2-cGMP-sensor cells (with Nppc).

Figure 9A:
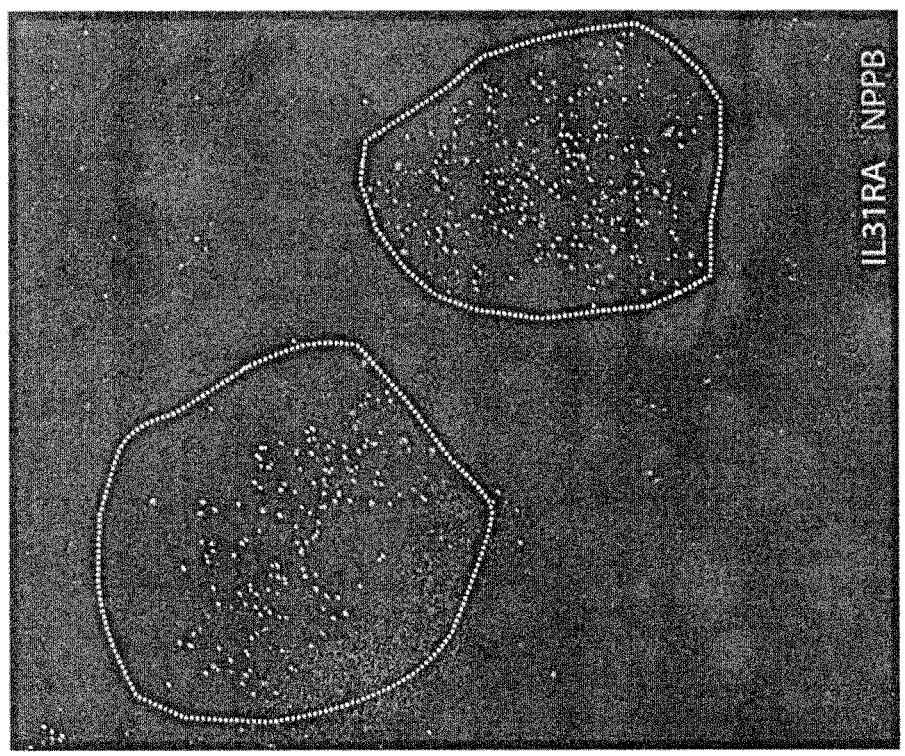

FIG. 9A is a photographic image of double-labelling ISH staining of human DRG sections revealed that NPPB and IL31RA (illuminated dots shown in side of white-doted circles) are co-expressed. The expression of Nppb was determined with development with a green amplified agent and IL31RA with a red agent. Red and green staining was present in the same neurons. DRG sections were counter-stained with DAPI (grey background). Neurons stained for Nppb and itch-receptors are highlighted within the white-dotted profile circles.

Figure 9B:
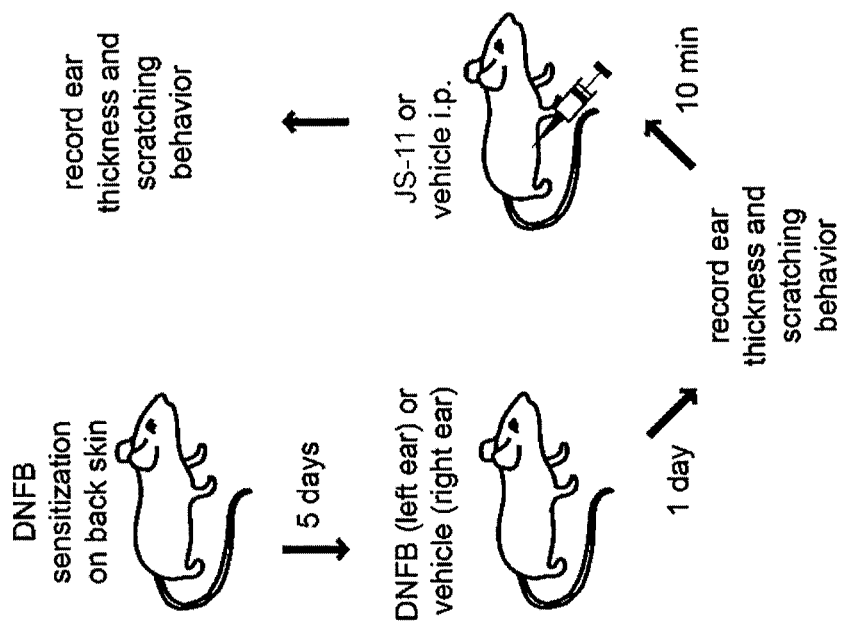

FIG. 9B is a schematic diagram of the experimental procedure for contact hypersensitivity-induced itch, according to embodiments of the invention.

Figure 9C:
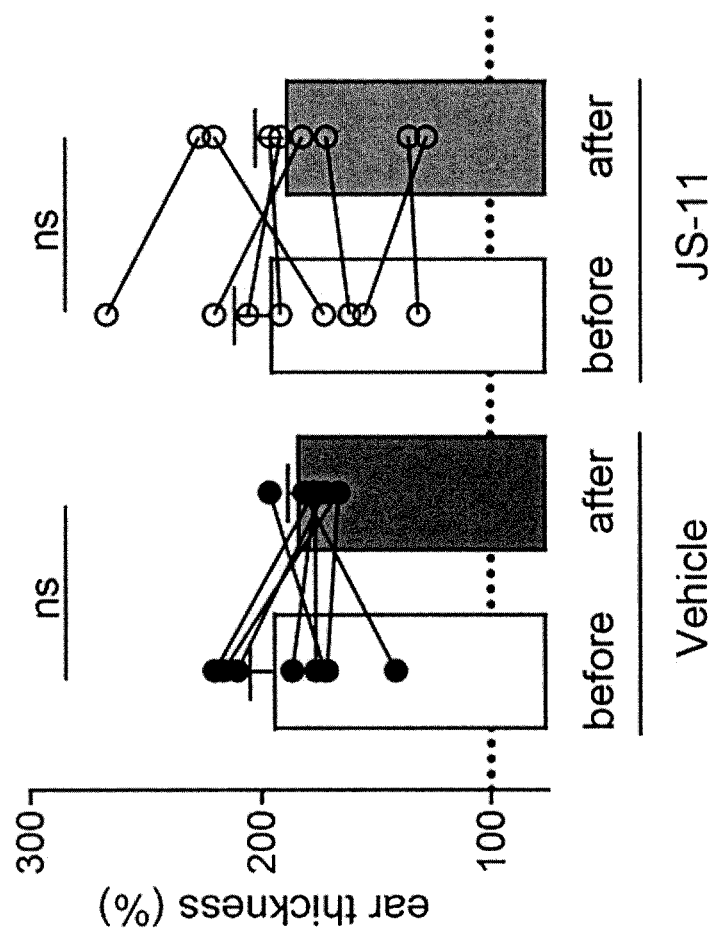

FIG. 9C is a plot showing that no differences in % ear thickness were detectable between JS-11 and vehicle-treated control mice. Differences were assessed using paired two-tailed Student's t-test (DMSO: ns P=0.3965, JS-11: ns P=0.5401). Data represent means SEM of n=8.

Figure 9D:
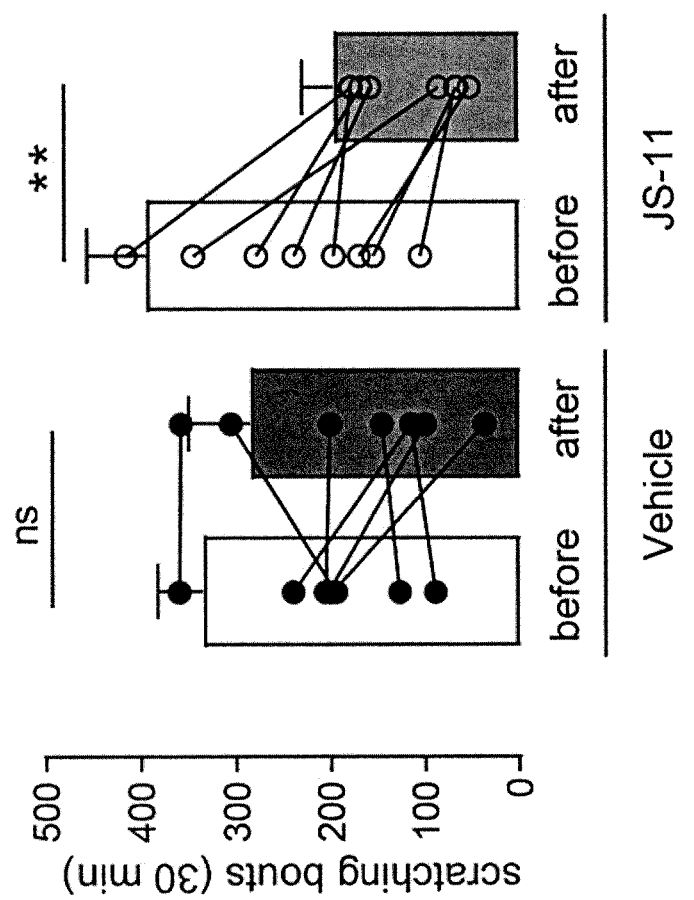

FIG. 9D is a plot showing that itch-behavior was significantly reduced by administration of JS-11. Differences were assessed using paired two-tailed Student's t-test (DMSO: ns P=0.3827, JS-11: *P=0.0061). Data represent means SEM of n=8.

DETAILED DESCRIPTION OF THE INVENTION

An embodiment of the invention provides a pharmaceutical composition comprising (a) a pharmaceutically acceptable carrier and (b) one or more molecular inhibitor(s) of Npr1. As used herein, unless stated otherwise, the terms "Nppb" and "Npr1" refer to Nppb and Npr1, respectively, in any form (e.g., mRNA or protein) and from any species (e.g., human or mouse). While, in the context of the invention, the molecular inhibitor can inhibit any mammalian Npr1, it is preferred that it inhibit the human isoform of Npr1, which is referred to herein as "hNpr1."

The pharmaceutically acceptable carrier for use in the inventive pharmaceutical composition can be any of those conventionally used and is limited only by chemico-physical considerations, such as solubility and lack of reactivity with the active compound(s), and by the route of administration.

The pharmaceutically acceptable carriers for use in the present invention—for example, vehicles, excipients, and diluents—are well-known to those skilled in the art and are readily available to the public. It is preferred that the pharmaceutically acceptable carrier be one which is chemically inert to the active agent(s) (i.e., the one or more a molecular inhibitor(s) of Npr1) and one which has no detrimental side effects or toxicity under the conditions of use. The choice of carrier will be determined in part by the particular compounds used in the pharmaceutical composition, as well as by the particular method used to administer the one or more molecular inhibitor(s) of Npr1.

The one or more molecular inhibitor(s) of Npr1 for use in the inventive pharmaceutical composition can be any molecular agent that inhibits the biological activity of Npr1 in any manner, e.g., by inhibiting the production (e.g., expression) of any one or more of Nppb mRNA and Nppb protein, or Npr1 mRNA and Npr1 protein; by inhibiting the binding of Nppb to Npr1 and/or by inhibiting Nppb or Npr1 signaling, as compared to that which is observed in the absence of the molecular inhibitor of Npr1. The biological activity may be inhibited to any degree that realizes a beneficial therapeutic effect. For example, in some embodiments, the biological activity may be completely inhibited (i.e., prevented), while in other embodiments, the biological activity may be partially inhibited (i.e., reduced). The inhibition of hNpr1 is measured by determining the reduced production of cGMP, as described herein with respect to other aspects of the invention.

In an embodiment of the invention, the molecular inhibitor of Npr1 is an agent that inhibits Npr1 signaling. In the context of the present invention, Npr1 signaling can be inhibited in any manner. For example, the molecular inhibitor of Npr1 may inhibit the activation of any one or more of various downstream targets of Nppb or Npr1 signaling. For example, the inhibitor of Npr1 may be an agent that binds to the Nppb protein, thereby reducing or preventing Nppb signaling and inhibiting its function. By way of illustration, the agent that inhibits Npr1 signaling can be a chemical inhibitor, such as, for example, any of the chemical inhibitors described herein. In a preferred embodiment, the molecular inhibitor of Npr1 is the molecular inhibitor described herein as compound JS-11, i.e., 1-cyclohexyl-3-(cyclopropylmethyl)-N-((3-methylisoxazol-5-yl)methyl)-2-oxo-2,3-dihydro-H-benzo[d]imidazole-5-carboxamide.

Molecular inhibitors of Npr1 include small molecules that inhibit Nppb and/or Npr1 signaling, bind the Nppb or Npr1 protein or functional fragment thereof, or compete with the Nppb protein or functional fragment thereof for its native binding site of the Npr1. Suitable inhibitors of Npr1 can include, for example, any one of the chemical compounds described herein.

A molecular inhibitor of Npr1 for use in the present invention can be identified, in one aspect, using high-throughput screening ("HTS") of chemical compounds. HTS is an automated drug-discovery process that quickly assays the biological or biochemical activity of a large number of chemical compounds (referred to herein as a "library) against a chosen set of defined targets. Screening large numbers of biological modulators across a library of targets produces a number of "active hits," or "actives" which can then be interrogated in detail through secondary hit validation. The actives of interest may be selected as potentially potent modulators for progression to additional, in-depth studies, and compounds with poor or no effect can be dropped from investigation. HTS may be used for discovering ligands for receptors, enzymes, ion-channels, antibodies or other pharmacological targets, or pharmacologically profiling a cellular or biochemical pathway of interest for pharmacological discovery (see e.g., Malo et al., *Nat. Biotechnol.,* 24: 167-175 (2006) (which is incorporated herein by reference in its entirety)). Typically, HTS assays are performed at a single concentration in microtiter plates with a 96, 384, or 1536 well format.

Alternatively, quantitative HTS or "qHTS" can be used to screen for biological modulators such as a molecular inhibitor of Npr1 for use in the present invention. Quantitative HTS utilizes advanced screening technologies, such as low-volume dispensing, high-sensitivity detectors, and robotic plate handling, to develop a titration-based screening approach (see, e.g., Inglese et al., *PNAS USA,* 103: 11473-11478 (2006) (which is incorporated herein by reference in its entirety) and Austin et al., *Science,* 306: 1138-1139 (2004) (which is incorporated herein by reference in its entirety)).

The HTS, qHTS, or other screening technologies typically involve screening a library of many compounds. Such full-scale HTS or qHTS libraries may extend into many thousands of compounds and/or constructs. Libraries are initially divided by composition—e.g. small compound, siRNA, shRNA, etc. Libraries may be further sub-divided into smaller libraries according to biological family or target specificity. Libraries are arrayed into micro-well plates enabling screening in a miniaturized format in 96, 384, and 1536 well plates. An exemplary library of compounds suitable for identifying the molecular inhibitors of Npr1 for use in the context of the current invention include the National Institutes of Health National Center for Advancing Translational Sciences ("NCATS") Genesis Chemical Library. This Genesis Chemical Library contains between 80,000 and 100,000 compounds. The collection is plated in qHTS format, enabling large-scale deorphanization of unprecedented mechanisms. The compounds within this Genesis Chemical Library originate from various sources/vendors. Without wishing to be bound, it is believed that most compounds in the Genesis Chemical Library can be purchased directly from the original vendors.

Preferably, one or more of the following compounds can be used in the context of the present invention:
(a) 4-(cyclohexylmethyl)-4,5-dihydrospiro[benzo[e][1,4]diazepine-3,4'-piperidin]-2(1H)-one hydrochloride (ChemRoutes Corporation, catalog number CA-42-206);
(b) 2-(4-chlorophenyl)-1-(1'-(pyrrolidin-3-ylmethyl)-1,5-dihydrospiro[benzo[c]azepine-4,2'-pyrrolidin]-2(3H)-yl) ethan-1-one (ChemRoutes Corporation, catalog number CA-21-113);
(c) N-(((2R,4S,5R)-5-(6-(pentan-3-yl)-2-(pyridin-4-yl)pyrimidin-4-yl)quinuclidin-2-yl)methyl)thiophene-2-sulfonamide (AnalytiCon Discovery, LLC, catalog number NAT13-341676);
(d) N-(1-(3-methoxy-5-(pyridin-4-yl)benzyl)-4-methylpiperidin-4-yl)acetamide (Charles River Discovery Research Services, catalog number 1318_3888_0069);
(e) 3,5-dimethyl-4-(6-(2-phenoxyphenyl)imidazo[1,5-a]pyridin-8-yl)isoxazole (Charles River Discovery Research Services, catalog number 1362_1108_0063);
(f) 3-(2-methoxyphenyl)-N-(pyridin-3-ylmethyl)-1H-pyrazolo[3,4-b]pyrazine-5-carboxamide (Charles River Discovery Research Services, catalog number 1427_0083_0263_4003);
(g) 3-phenyl-N-(pyridin-3-ylmethyl)-1H-pyrazolo[3,4-b]pyrazine-5-carboxamide (Charles River Discovery Research Services, catalog number 1427_0061_0263_4003);
(h) 2-(benzo[d][1,3]dioxol-5-yl)-1-(3-(2-(benzyloxy)phenyl)-2-methyl-6,7-dihydropyrazolo[1,5-a]pyrimidin-4 (5H)-yl)ethan-1-one carboxamide (Charles River Discovery Research Services, catalog number 1449_0064_0655);
(i) 1-(3-(2-(benzyloxy)phenyl)-2-methyl-6,7-dihydropyrazolo[1,5-a]pyrimidin-4(5H)-yl)-2-(pyridin-2-yl)ethan-1-one (Charles River Discovery Research Services, catalog number 1449_0064_0670);
(j) 2-(benzo[d][1,3]dioxol-5-yl)-1-(2-methyl-3-(2-phenoxyphenyl)-6,7-dihydropyrazolo[1,5-a]pyrimidin-4(5H)-yl) ethan-1-one (Charles River Discovery Research Services, catalog number 1449_0063_0655);
(k) 1-cyclohexyl-3-(cyclopropylmethyl)-N-((3-methylisoxazol-5-yl)methyl)-2-oxo-2,3-dihydro-1H-benzo[d]imidazole-5-carboxamide (Chembridge Corporation, catalog number 65833004);
(l) (1-(4-methoxyphenyl)cyclopropyl)(5-methyl-5,6-dihydrospiro[benzo[f]imidazo[1,2-a][1,4]diazepine-4,4'-piperidin]-1'-yl)methanone (Chemdiv Inc., catalog number S217-0244);
(m) N-benzyl-1-(2-cyanobenzyl)-4-oxo-1,5-diazacycloundecane-8-carboxamide (Chemdiv Inc., catalog number S733-0866); or
(n) N-benzyl-N-methyl-8-phenylimidazo[1,2-a]pyrazine-2-carboxamide (Chemdiv Inc., catalog number T425-0460). See Table 1 for additional information about compounds for use in the context of the present invention.

In a preferred embodiment, the following compound can be used in the context of the present invention:
1-cyclohexyl-3-(cyclopropylmethyl)-N-((3-methylisoxazol-5-yl)methyl)-2-oxo-2,3-dihydro-1H-benzo[d]imidazole-5-carboxamide (Chembridge Corporation, catalog number 65833004).

In a particular, and non-limiting, embodiment, the invention provides a pharmaceutical composition comprising (a) a pharmaceutically acceptable carrier and (b) one or more of the foregoing compounds ("(a)" through "(n)") and/or one or more of the compounds identified as "JS1" through "JS14" in Table 1. Such compounds are present within the aforementioned Genesis Chemical Library and can be obtained commercially from the vendors provided herein. In some embodiments, the inventive composition (including its use in the inventive methods described herein) includes only compounds selected from the list identified above ("(a)" through "(n)") and/or one or more of the compounds identified as "JS1" through "JS14" in Table 1. In a particular embodiment, the invention provides a pharmaceutical composition comprising (a) a pharmaceutically acceptable carrier and (b) the compound identified as "JS-11" in Table 1, i.e., 1-cyclohexyl-3-(cyclopropylmethyl)-N-((3-methylisoxazol-5-yl)methyl)-2-oxo-2,3-dihydro-TH-benzo[d]imidazole-5-carboxamide. JS-11 is present within the aforementioned Genesis Chemical Library and can be obtained commercially from the vendor provided herein. In a preferred embodiment, the composition as herein described is for use in the treatment, reduction, or prevention of acute and/or chronic pruritus in a mammal.

In another embodiment, the invention provides a method of treating, reducing, or preventing acute and/or chronic pruritus in a mammal comprising administering a pharmaceutical composition (for example, as described above) comprising (a) a pharmaceutically acceptable carrier and (b) a molecular inhibitor of Npr1; thereby treating, reducing, or preventing acute and/or chronic pruritus in the mammal. Accordingly, the invention provides a pharmaceutical composition comprising (a) a pharmaceutically acceptable carrier and (b) a molecular inhibitor of Npr1, as herein described, for use in the treatment, reduction, or prevention of acute and/or chronic pruritus in a mammal. Further, it will be observed that the invention encompasses the use of a molecular inhibitor of Npr1, as herein described, for the preparation of a medicament, preferably one suitable for the treatment, reduction, or prevention of acute and/or chronic pruritus in a mammal.

The pruritus may be caused by or associated with any condition or any treatment of a condition. In an embodiment of the invention, the pruritus may be caused by or associated with a skin condition. Examples of skin conditions may include, but are not limited to, skin infections from *Trichomonas* or a fungus, psoriasis, and atopic dermatitis (also known as eczema). In an embodiment of the invention, the pruritus may be caused by or associated with a systemic condition or treatment of a systemic condition. Examples of systemic conditions may include, but are not limited to, renal failure, liver damage, liver disease (e.g., cirrhosis), acquired immune deficiency syndrome (AIDS), polycythemia vera, diabetes, hyperthyroidism, and cancer (e.g., Hodgkin's lymphoma, non-Hodgkin's lymphoma, and Kaposi's sarcoma). Examples of treatments of systemic conditions include, but are not limited to, kidney dialysis and chemotherapy with agents such as, for example, doxorubicin, daunorubicin, cytarabine, paclitaxel, and cisplatin. These chemotherapeutic agents, which are used to treat a variety of cancers, may cause a skin reaction and may be associated with pruritus. The incidence of non-cancer causes of pruritus may depend on the condition and type of treatment.

In an embodiment of the invention, the pruritus is induced by a pruritogen, for example, histamine, chloroquine, endothelin (ET-1), 2-methyl serotonin (5HT), SLIGRL-NH2 (PAR2), and compound 48/80 (48/80).

Also, the pruritus may be induced by a cytokine. In an embodiment of the invention, the pruritus is induced or mediated by interleukin (IL)-31. IL-31 is associated with chronic itch in some types of skin disorders such as, for example, atopic dermatitis.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of pruritus in a mammal. Furthermore, the treatment or prevention provided by the inventive method can include treatment or prevention of one or more conditions or symptoms of the pruritus, e.g., chronic pruritus, being treated or prevented. Also, for purposes herein, "prevention" can encompass delaying the onset of the pruritus, or a symptom or condition thereof. With respect to the inventive methods, the pruritus can be any pruritus, including any of the types of pruritus caused by or associated with any of the conditions or treatments discussed herein.

For purposes of the invention, the amount or dose of the molecular inhibitor of Npr1 administered should be sufficient to effect the desired biological response, e.g., a therapeutic or prophylactic response, in the mammal over a clinically reasonable time frame. The dose will be determined by the efficacy of the particular molecular inhibitor of Npr1 and the condition of the mammal (e.g., human), as well as the body weight of the mammal (e.g., human) to be treated. The dose of the molecular inhibitor of Npr1 also will be determined by the existence, nature and extent of any adverse side effects that might accompany the administration of a particular molecular inhibitor of Npr1.

Typically, the attending physician will decide the dosage of the molecular inhibitor of Npr1 with which to treat each individual patient, taking into consideration a variety of factors, such as age, body weight, general health, diet, sex, molecular inhibitor of Npr1 to be administered, route of administration, and the severity of the condition being treated. The dose, or dosage, of a pharmaceutical composition of the present invention may be appropriately determined by considering the dosage form, method of administration, patient age and body weight, symptoms of the patient, or severity of the condition. Generally, the daily dose for an adult can be, e.g., between 0.1 mg to 10,000 mg at once or in several portions. The dose can be, e.g., 0.2 to 10,000 mg/day (e.g., 1-10 g/day, 2-8 g/day, 1-5 g/day, 0.5 to 2.5 g/day, 0.5 to 500 mg/day, 1 to 300 mg/day, 3 to 100 mg/day, or 5 to 50 mg/day). These doses, or dosages, may vary, depending on the patient body weight and age, and the method of administration; however, selection of suitable dose, or dosage, is well within the purview of those skilled in the art. Similarly, the dosing period may be appropriately determined depending on the therapeutic progress. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. The mammal can be non-diseased, a mammal afflicted with pruritus, or a mammal predisposed to pruritus.

In an embodiment of the invention, administering the molecular inhibitor of Npr1 to the mammal may comprise administering the molecular inhibitor of Npr1 orally, intravenously, intramuscularly, subcutaneously, or intraperitoneally. The following formulations for oral, intravenous, intramuscular, subcutaneous, or intraperitoneal administration are exemplary and are in no way limiting. More than one route can be used to administer the molecular inhibitor of Npr1, and in certain instances, a particular route can provide a more immediate and more effective response than another route.

Oral formulations may include any suitable carrier. For example, formulations suitable for oral administration may comprise suitable carriers, such as lactose, sucrose, starch, talc magnesium stearate, crystalline cellulose, methyl cellulose, carboxymethyl cellulose, glycerin, sodium alginate or gum arabic among others.

Intravenous, intramuscular, subcutaneous, or intraperitoneal formulations may include any suitable carrier. For example, formulations suitable for intravenous, intramuscular, subcutaneous, or intraperitoneal administration may comprise sterile aqueous solutions of the molecular inhibitor of Npr1 with solutions which are preferably isotonic with the blood of the recipient. Such formulations may be prepared by dissolving the molecular inhibitor of Npr1 in water or other suitable physiologically acceptable solvent containing physiologically compatible substances such as sodium chloride (e.g. 0.1-2.0M), glycine, and the like, and having a buffered pH compatible with physiological conditions to produce solution (e.g., an aqueous solution or solution of the molecular inhibitor of Npr1 in a suitable physiologically acceptable solvent), and rendering said solution sterile.

The following examples further illustrate the invention but, of course, should not be construed as in any way limiting its scope. In the context of these examples, the term "NppA" refers to natriuretic peptide A, a paralog of NppB, which also acts on the Npr1 receptor. As used herein, the term "NppC" refers to natriuretic peptide C, a second paralog of NppB, which also acts on the Npr1 receptor. Also, the term Npr2 refers to natriuretic peptide receptor 2, the second integral membrane receptor for natriuretic peptides in addition to Npr1, which is discussed herein with respect to other aspects of the invention. Npr2 receptor is related to the Npr1 receptor. Without wishing to be bound, the while Npr1 and Npr2 receptors are related, the agents that stimulate the Npr1 and Npr2 receptors are quite different. For example, for Npr1, NppA is a very strong stimulator (agonist), while NppC is a very weak agonist. The reverse is true for Npr2, i.e., NppC is a strong agonist, while NppA is very weak.

Example 1

In order to identify small molecular compounds that inhibit the Npr1 receptor a high-throughput assay to probe inhibition of the receptor guanylate cyclase Npr1 was developed. The assay was designed taking advantage of Promega's GloSensor™ technology (Promega, Madison, Wis.). This technology involves the expression of a cyclic guanosine monophosphate (cGMP) biosensor, comprised of a firefly luciferase variant that was coupled to the cGMP binding domain of human phosphodiesterase 5A, and loading of cells with a cell-permeable luciferase substrate to monitor cGMP production by Npr1 in real time in live cells. Briefly, human embryonic kidney 293 cells stably expressing the human Npr1 and the pGloSensor™-40F cGMP vector ("pGloSensor™-40F") were generated. Stimulating these cells with the Npr1 agonists human NppA or NppB, luciferase-induced light production could be detected in a dose-dependent manner. HEK293 cells stably expressing human Npr2 and pGS-40F and cells only expressing pGS-40F were also generated to conduct secondary counter screens. In these cells, NppC or sodium nitroprusside were used to stimulate Npr2 or soluble guanylate cyclase which is endogenously expressed in HEK293 cells, respectively. The Npr2-NppC counter screen was employed to search for agents that minimally effected this agonist-receptor interaction. The Npr2-NppC system was used because the side effects of most drugs occur on related receptors. Npr1 and Npr2 are the most related receptors in sequence and function and there are no additional active receptor subtypes in this family of receptors. The procedure is described in detail below.

Materials

Nppa, murine Nppa, and A-71915 were purchased from Bachem (Torrance, Calif.). Human Nppb, CYM5442 and Histamine were purchased from Tocris (Minneapolis, Minn.), murine Nppb was from Peptide 2.0 (Chantilly, Va.), and Nppc was from Mimotopes (Raleigh, N.C.). JS-3 was purchased from Analyticon Biotechnologies (Lichtenfels, Germany), JS-4-JS-10 were purchased from Charles River Discovery (Franklin, Mass.), JS-11 was from Chembridge (San Diego, Calif.), and JS-12-JS-14 were from Chemdiv (San Diego, Calif.). If not indicated otherwise, all other reagents were purchased from ThermoFisher (Waltham, Mass.) or Sigma-Aldrich (St. Louis, Mo.).

In Situ Hybridization

DRGs from 3 different, healthy donors were obtained from the Tissue For Research website and the NIH Neuro-BioBank at the University of Maryland (Baltimore, Md.). Mouse DRGs were dissected from C57BL/6N mice (Envigo, Indianapolis, Ind.). ISH staining was performed using the RNAscope® (ACD, Newark, Calif.) technology according to the manufacturer's instructions. Probes specific for hTRPV1, hNPPB, hHRH1, hMRGPRX1, hIL31RA, mTrpV1, and mNppb in conjunction with the RNAscope® multiplex fluorescent development kit were used and nuclei were counter-stained using DAPI. Since human tissue has high auto-fluorescence, to quench auto-fluorescence after the staining procedure, DRG sections were consecutively treated with TrueView™ (Vector laboratories, Burlingame, Calif.) and TrueBlack® (Biotium, Fremont, Calif.). Images were collected on an Eclipse Ti (Nikon, Melville, N.Y.) confocal laser-scanning microscope using a 40× objective and to enhance visibility of the ISH signals, residual auto-fluorescent signal was background-subtracted with Image J (NIH, Bethesda, Md.).

Eukaryotic Expression Vectors

The pGloSensor™-40F cGMP vector and coding for a cGMP biosensor, was purchased from Promega (Madison, Wis.). Expression vectors for murine and human Npr1, MC223390 and SC125506, respectively, were purchased from OnGene Technologies (Rockville, Md.). ADDGENE plasmid #23479 (pDONR223-NPR2) (Cambridge, Mass.) was obtained as a gift to the laboratory. The sequence coding for human Npr2 was subcloned into the expression vector pCMV6-ENTRY (OnGene Technologies) using standard molecular biology methodology. The generation of pEAK8-GFP is described in Mishra et al., *J. Neurosci.*, 32: 8686-8695 (2012) (which is incorporated herein by reference in its entirety).

Cell Culture and Transfection

HEK-293 cells (American Type Culture Collection "ATTC," Manassas, Va.) were cultured in DMEM/F12 supplemented with 2 mM L-glutamine, 10% FBS, 100 U/ml penicillin, and 100 µg/ml streptomycin. For transient expression, $8 \times 10^5$ cells were seeded in 6-wells, cultured for 24 hours, and then transfected using TransIT®-293 (Mirus, Madison, Wis.) according to the manufacturer's instructions. After transfection (48 hours), cells were used to measure intracellular cGMP production. HEK-293 cell clones stably expressing pGloSensor™-40F alone (HEK-cGMP-sensor cells) or in addition, human Npr1 ("hNpr1") (HEK-hNpr1-cGMP-sensor cells) or human Npr2 (HEK-hNpr2-cGMP-sensor cells) were generated by co-transfection with pEAK8-GFP and selection with 1 µg/ml puromycin. Stable expression of transgenes was verified by measuring ligand-induced cGMP production with the cGMP biosensor.

Measurement of Intracellular cGMP Production

Before the measurement (24 hours in advance), $3 \times 10^4$ cells were seeded into white 96-well plates (PerkinElmer, Waltham, Mass.), coated with 0.1% poly(D-lysine), and assays conducted as recommended by the manufacturer (Promega). Medium was aspirated and cells were loaded for two hours at room temperature with 2% GoSensor™ reagent diluted in $CO_2$-independent media (ThermoFisher) supplemented with 2 mM L-glutamine and 10% FBS (assay medium). Luminescence was measured on a BioTek Synergy™ NEO (Winooski, Vt.) plate reader at room temperature. After a baseline measurement of 3-5 minutes, assay medium as a control or assay medium with agonist was manually added, and luminescence was measured for 30 minutes at ~1/60 Hz. For compounds tested for Npr1 and Npr2 inhibition, the compounds were added after baseline measurements, and luminescence was read for 5 minutes before addition of agonist. Luminescence was then normalized to baseline measurements and plotted against the time. Ligand-induced changes of cGMP production were quantified by determining the area under the curve. To determine efficacy and potency of agonists, ligand-induced changes were normalized to medium only addition and plotted against the ligand concentration. To determine efficacy and potency of agonists, ligand-induced changes were normalized to vehicle addition and plotted against the ligand concentration. To quantify efficacy ($IC_{50}$) and potency ($I_{max}$) of compounds, compound-induced changes of agonist-induced cGMP production were normalized to vehicle controls, plotted against compound concentration, and fit with a four-parameter logistic regression. Effects of A-71915 on basal mNpr1 activity were fitted with a bell-shaped regression (equation indicated below).

Genesis Library Preparation

The Genesis library consisted of 86,437 compounds at the time of screening. Samples of all 86,437 library compounds were plated into 384-well plates (Greiner Bio-One, Monroe, N.C.) comprising a 7-point inter-plate titration with a serial dilution of 1:5 in DMSO ranging from 10 mM to 640 µM. Plates were reformatted in quadrants into 1536-well format using an EVOLUTION P3 System (PerkinElmer).

Quantitative HTS

Measurement of intracellular cGMP production in HEK-hNpr1-cGMP-sensor cells was scaled to 4 µl volumes in 1536-well format and primary screening was performed in an automated manner in 7- to 11-point qHTS. Cells ($1.5 \times 10^3$) were plated in assay medium in white, solid bottom TC treated 1536-well plates (Greiner Bio-One) with a Multidrop™ Combi Reagent Dispenser (Thermo Fisher Scientific). Cells were incubated at 37° C., 5% $CO_2$ and 95% humidity for 16 hours and 1 µl of GloSensor™ reagent at a final assay concentration of 2% or assay medium as background control was added to respective wells with a BioRAPTR Flying Reagent Dispenser™ (Beckman Coulter, Schaumburg, Ill.). Cells were incubated at room temperature for 2 hours, protected from light. Compound (23 nl) was transferred by a pintool (Kalypsys, San Diego, Calif.) in the concentration range of 3.0 µM to 46.1 µM along with DMSO and a titration of A-71915 from top concentration 38.3 µM to 1.7 nM in columns 1-4 of each plate as vehicle and positive controls, respectively. Cells were incubated with compound for 30 minutes at room temperature, protected from light. Pre-agonist luminescence for each plate was read on a ViewLux™ plate reader (PerkinElmer). Human NppA (1 µl) at a final assay concentration of 0.1 nM, or C02-independent media were added to respective wells with a BioRAPTR Flying Reagent Dispenser™ (Beckman Coulter). Plates were incubated for 20 minutes at room temperature, protected from light, and luminescence was read on a ViewLux™ plate reader.

Pre-agonist and post-agonist data were normalized by plate to corresponding intra-plate controls as described in Inglese et al., *PNAS USA*, 103: 11473-11478 (2006) (which is incorporated herein by reference, in its entirety). Assay statistics including S:N and Z' were calculated using the same respective controls. Pre-agonist data were normalized to the average signal of DMSO-treated wells with 2% GoSensor™ reagent as 0% and the average signal of DMSO-treated wells with assay medium as –100% activity. Post-agonist data were normalized to the average signal of DMSO-treated wells with 2% GoSensor™ reagent and 0.1 nM hNppA as 0% and the average signal of wells treated with 38.3 µM A-71915 with 2% GloSensor™ reagent and 0.1 nM hNppA as –100% activity. The respective normalized data from each assay plate was corrected using DMSO only treated assay plates at the beginning and end of the screen and interspersed every 20-30 plates throughout screening. In-house software was used to fit the resulting inter-plate titration data to the standard hill equation and concentration-response curves were classified by activity. Curve fit assignments of 1.1, 1.2, 2.1, and 2.2 were considered active and visually confirmed. These data were refit in GraphPad Prism™ 7.0 (GraphPad Software, Inc., La Jolla, Calif.) with nonlinear regression log(agonist) vs. response-variable slope (four parameters) fit. Bell-shaped curves were fit in Graphpad Prism™ 7.0 (GraphPad) with nonlinear regression and the equation:

$$Y = S0 + \frac{(S1-S0)}{(1+10^{((logEC50-X)*HillSlope\,1)})} + \frac{(S2-S1)}{(1+10^{((logIC50-X)*HillSlope\,2)})}$$

qHTS Follow-Up of Actives

Active molecules were prioritized based on post-agonist concentration-response curves, maximum efficacy and potency with minimal activity in the corresponding pre-agonist data. The compounds selected for follow-up, 1,408 compounds in total, were replated in 11-pt inter-plate titration with a serial dilution of 1:3 in DMSO ranging from 10 mM to 169 µM. The primary screening assay was repeated with the follow-up compounds as described above. Four different counter screens were conducted to eliminate false positive compounds.

To account for compounds selected because of their inhibition in qHTS, but which selection may have been dependent on interference with components of the assay rather than direct inhibition of hNpr1, several overlapping strategies were used to identify bona fide hNpr1 inhibitors and eliminate false positives, including conducting the four different counter screens described below. First, hNpr1 assays were repeated, at 11 concentrations on all selected compounds, to validate all positive compounds from the primary screen. This confirmed the selection criteria used for the selection of the active compounds. Compounds which interfered directly with luciferase, or molecules which are cytotoxic were subtracted using two different assays as described in Jang, et al. "Identification of drug modulators targeting gene-dosage disease CMT1A," *ACS Chem Biol* 7, 1205-1213 (2012), which is herein incorporated by reference. Third, to eliminate compounds that directly blocked cGMP sensor activity, or sequestered the GloSensor™ reagent, the selected compounds were tested for the inhibition of luciferase activity upon activating soluble guanylate cyclases in HEK293-cGMP sensor cells (using sodium nitroprusside "SNP"). The counter-screens eliminated most compounds with only 20 candidates remaining after all screens were completed. Characteristics of fourteen of these candidates are provided in the tables below.

HEK293-hNpr2-cGMP-Sensor and HEK293-cGMP-Sensor Cells Counter Screens

Counter-screens were performed with HEK293-hNpr2-cGMP-sensor and HEK293-cGMP-sensor cells. These cells were stimulated with 1 nM NppC or 50 µM sodium nitroprusside, respectively, but otherwise the assay was conducted as described for HEK-hNpr1-cGMP-sensor cells. Pre-agonist controls were the same for all three assays, but normalization of post-agonist data differed between assays. For HEK-hNpr1-cGMP-sensor cells, –100% activity in post-agonist data was defined as described for primary screening, while for HEK-hNpr2-cGMP-sensor and HEK-cGMP-sensor cells, the average signal of DMSO-treated wells with 2% GloSensor™ reagent and the respective agonist was defined as 0% and the average signal of wells without agonist as −100% activity and data were normalized accordingly. Compounds directly interacting with the pGloSensor™-40F reporter system in HEK293 cells stimulated with sodium nitroprusside were eliminated as false positives. Effects of compounds on HEK293 cells stimulated with NppC and stably expressing hNpr2 and pGS-40F were tested for receptor selectivity.

Cytotoxicity Counter-Screen

Compound cytotoxicity was tested with Promega's CellTiter-Glo™ assay which measures cellular adenosine triphosphate content, a surrogate of metabolic activity, with a firefly luciferase reagent. A cytotoxicity counter-screen using HEK-hNpr1-cGMP-sensor cells was performed on the 1,408 follow-up compounds. Cells ($1.5 \times 10^3$) cells were plated in 4 µL C02-independent media in white, solid bottom TC-treated 1536-well plates (Greiner Bio-One). Cells were incubated at 37° C., 5% $CO_2$ and 95% humidity for 16 hours. Compound transfer was performed as described for qHTS along with DMSO and a titration of Digitonin from a top concentration of 115 µM to 3.5 nM in columns 1-4 of each assay plate as vehicle and cytotoxicity controls, respectively. Cells were incubated with compound for 2 hours at 37° C. CellTiter-Glo™ reagent (Promega) (3 µl) was added to each well with a BioRAPTR Flying Reagent Dispenser™ (Beckman Coulter) and plates were incubated for 10 min at room temperature, protected from light. Luminescence was measured on a ViewLux™ plate reader. Data were normalized to the average signal of DMSO-treated wells as 0% and the average signal of wells treated with 115 µM Digitonin as −100% activity and analyzed as above.

Biochemical Firefly Luciferase Enzymatic Counter-Screen

Direct effects of compounds on firefly luciferase enzymatic activity were tested in vitro. A Firefly luciferase enzyme assay was performed on the 1,408 follow-up compounds. To achieve half-maximal reaction velocity, the D-Luciferin substrate concentration equaled Km and the assay was otherwise performed according to Jang et al., *ACS Chem. Bio.*, 7: 1205-1213 (2012) (which is incorporated herein by reference, in its entirety), as follows: 3 µl of substrate-buffer solution (0.01 mM D-Luciferin, 0.01 mM ATP, 50 mM Tris Acetate, 10 mM Mg Acetate, 0.01% Tween-20 and 0.038% BSA final concentrations) were dispensed into white, solid bottom medium bind 1536-well plates (Greiner Bio-One) with a BioRAPTR Flying Reagent Dispenser™ (Beckman Coulter). Compounds were transferred as described for qHTS along with DMSO (as a negative control) and titrations of PTC124 (as a positive control), ranging from the top concentration of 57.5 µM to 4.0 µM in columns 1-4 of each plate as vehicle and positive controls, respectively. Luciferase enzyme-buffer solution (1 µl) (10 nM *P. pyralis* luciferase in 50 mM Tris Acetate final concentration) was dispensed and after a 5-minute incubation at room temperature, luminescence was read on a ViewLux™ plate reader. Data were normalized to the average signal of DMSO-treated wells as 0% (which indicates that the tested compound does not inhibit luciferase in the assay) and the average signal of wells treated with 57.5 µM PTC124 as −100% activity (which indicates that the tested compound is inhibiting luciferase in the assay) and processed as above.

Membrane Fractionation

Two days before membrane fractionation, $8 \times 10^6$ HEK-hNpr1-cGMP-sensor cells or HEK-hNpr2-cGMP-sensor cells were seeded in 150 mm dishes to grow to confluence. Medium was aspirated and cells were washed with ice-cold PBS without $Ca^{2+}/Mg^{2+}$. Cells were scraped loose in ice-cold 2.5 ml homogenization buffer (HEPES 50 mM, EDTA 5 mM, NaCl 50 mM, NaF 50 mM, microcystin 250 nM, glycerol 20%, cOmplete™ Ultra Mini protease inhibitor cocktail) with a rubber policeman and lysed with a glass-Teflon homogenizer on ice. To remove debris, the lysate was spun for 10 minutes at 500×g and 4° C. While the supernatant was stored on ice, the pellet was lysed again with a glass-Teflon homogenizer and centrifuged again for 10 minutes at 500×g and 4° C. Both supernatants were pooled and spun for 60 minutes at 100,000×g and 4° C. in an Optima™ XL-90 Ultracentrifuge (Beckman Coulter) equipped with a 70-Ti rotor. The supernatant was discarded and the pellet was resuspended in membrane buffer (HEPES 10 mM, EDTA 1 mM, microcystin 250 nM, cOmplete™ Ultra Mini protease inhibitor cocktail) by passing it through a 25 ga needle multiple times. Protein content in these membrane fractions was assessed by a Pierce™ BCA Protein assay kit (ThermoFisher) according to the manufacturer's instructions. Membranes were aliquoted to 100 µg protein, flash frozen in liquid nitrogen, and stored at −80° C.

Measurement of Npr1 Enzymatic Activity in Membrane Fractions

For measurement of Npr1 cyclase activity, per single reaction, 2 µg of membranes were diluted to 20 µl with $H_2O$ and mixed with 2.5 µl compound to incubate for 5 minutes. Then, the enzymatic reaction was started by adding pre-warmed 25 µl 12-fold concentrated assay buffer (HEPES 25 mM, EDTA 1 mM, ATP 1 mM, $MgCl_2$ 5 mM, microcystin 500 µM, GTP 2 mM final concentrations) with and without Npr1/2 agonist and allowed to proceed for 5 minutes at 37° C. The reaction was stopped by addition of 19.3 µl of 1 M hydrochloric acid and mixing on a shaker for 10 minutes. Samples were diluted appropriately and analyzed for cGMP content using a competitive colorimetric immunoassay (ADI-901-014, Enzo Life Sciences, Farmingdale, N.Y.) according to the manufacturer's instructions. To account for differences in cGMP content of starting material, a mock reaction that lacked the substrate GTP was performed and subtracted from experimental samples. To quantify efficacy ($IC_{50}$) and potency ($I_{max}$) of compounds, compound-induced changes of agonist-induced cGMP production were normalized to vehicle controls, plotted against the compound concentration, and data was fit with a four-parameter logistic regression.

Kinetic Solubility Assay

The µSOL assay was used for kinetic solubility determination, as described in Avdeef, et al., "Drug absorption in vitro model: filter-immobilized artificial membranes. 2. Studies of the permeability properties of lactones in *Piper methysticum* Forst," *Eur J Pharm Sci* 14, 271-280 (2001), which is incorporated by reference herein. In this assay, the classical saturation shake-flask solubility method was adapted as described. Test compounds were prepared as 10 mM DMSO stock solutions and diluted to a final compound concentration of 150 µM in aqueous solution (pH 7.4, 100 mM phosphate buffer). Samples were incubated at room temperature for 6 hours and vacuum-filtered using Te-Vac (Tecan, Morrisville, N.C.) to remove any precipitates. The concentration of the compound in the filtrate was measured via UV absorbance (k 250-498 nm). The unknown compound concentration was determined by comparing the fully solubilized reference plate which contained 17 μM of compound dissolved in spectroscopically pure n-propanol. All compounds were tested in duplicates. The kinetic solubility (μg/mL) of compounds was calculated using the pSOL Evolution software (Pion Inc., Billerica, Mass.). The three controls used were albendazole (low solubility), phenazolpyridine (moderate solubility) and furosemide (high solubility).

Rat Liver Microsome Stability Assay

Single time point microsomal stability was determined in a 96-well HTS format. Sample preparation was automated using an EVO 200 robot (Tecan, Switzerland). A high-resolution LC/MS (Thermo QExactive, ThermoFisher (Waltham, Mass.)) instrument was used to measure the percentage of compound remaining after incubation using a known method. Six standard controls were tested in each run: buspirone and propranolol (for short half-life), loperamide and diclofenac (for short to medium half-life), and carbamazepine and antipyrine (for long half-life). Briefly, the incubation consisted of 0.5 mg/mL microsomal protein, 1.0 μM compound concentration, and NADPH regeneration system (containing 0.650 mM NADP+, 1.65 mM glucose 6-phosphate, 1.65 mM $MgCl_2$, and 0.2 U/mL G6PDH) in 100 mM phosphate buffer at pH 7.4. The incubation was carried out at 37° C. for 15 min. The reaction was quenched by adding 555 μL of acetonitrile (1:2 ratio) containing 0.28 μM albendazole (internal standard).

Parallel Artificial Membrane Permeability Assay (PAMPA)

Stirring double-sink PAMPA method was employed to determine the permeability of compounds via PAMPA. The PAMPA lipid membrane consisted of an artificial membrane of a proprietary lipid mixture and dodecane (Pion Inc., Billerica, Mass.), optimized to predict gastrointestinal tract passive permeability. The lipid was immobilized on a plastic matrix of a 96-well "donor" filter plate placed above a 96-well "acceptor" plate. pH 7.4 solution was used in both donor and acceptor wells. The test articles, stocked in 10 mM DMSO solutions, were diluted to 0.05 mM in aqueous buffer (pH 7.4), and the concentration of DMSO was 0.5% in the final solution. During the 30-minute permeation period at room temperature, the test samples in the donor compartment were stirred using the Gutbox technology (Pion Inc.) to reduce the aqueous boundary layer. The test article concentrations in the donor and acceptor compartments were measured using a UV plate reader (Nano Quant, Infinite® 200 PRO, Tecan). Permeability calculations were performed using Pion Inc. software and were expressed in units of 10-6 cm/s. Compounds with low or weak UV signal were analyzed using high resolution LC/MS (Thermo QExactive, Thermo Fisher).

The potency of inhibition in both GoSensor™ and biochemical assays as well as the chemical structure of each compound are summarized in Table 1.

TABLE 1

| Abr name | IUPAC name | SMILES | IC$_{50}$ GloSensor™ assay (M) | IC$_{50}$ biochem assay (M) |
|---|---|---|---|---|
| JS1 | 4-(cyclohexylmethyl)-4,5-dihydrospiro[benzo[e][1,4]diazepine-3,4'-piperidin]-2(1H)-one hydrochloride | Cl•O=C1NC2=CC=CC=C2CN(CC3CCCC3)C14CCNCC4 | 7.31E−06 | not determined |
| JS2 | 2-(4-chlorophenyl)-1-(1'-(pyrrolidin-3-ylmethyl)-1,5-dihydrospiro[benzo[c]azepine-4,2'-pyrrolidin]-2(3H)-yl)ethan-1-one | ClC1=CC=C(CC(=O)N2CC3=CC=CC=C3CC4(CCCN4CC5CCNC5)C2)C=C1 | 1.30E−05 | not determined |
| JS3 | N-(((2R,4S,5R)-5-(6-(pentan-3-yl)-2-(pyridin-4-yl)pyrimidin-4-yl)quinuclidin-2-yl)methyl)thiophene-2-sulfonamide | CCC(CC)c1=NC(=NC(=C1)[C@H]2CN3CC[C@@H]2CN[S+]([O−])(=O)C4=CC=CS4)C5=CC=NC=C5 | 1.41E−05 | 3.98E−06 |
| JS4 | N-(1-(3-methoxy-5-(pyridin-4-yl)benzyl)-4-methylpiperidin-4-yl)acetamide | COC1=CC=CC(CN2CCC(C)(CC2)NC(C)=O)=C1C3=CC=NC=C3 | 1.41E−05 | 2.20E−06 |
| JS5 | 3,5-dimethyl-4-(6-(2-phenoxyphenyl)imidazo[1,5-a]pyridin-8-yl)isoxazole | CC1=C(C(C)=NO1)C2=CC(=CN3C=NC=C23)C4=CC=CC=C4OC5=CC=CC=C5 | 2.82E−05 | 1.41E−07 |
| JS6 | 3-(2-methoxyphenyl)-N-(pyridin-3-ylmethyl)-1H-pyrazolo[3,4-b]pyrazine-5-carboxamide | COC1=CC=CC=C1C2=NNC3=C2N=C(C=N3)C(=O)NCC4=CC=CN=C4 | 1.12E−05 | 7.66E−07 |
| JS7 | 3-phenyl-N-(pyridin-3-ylmethyl)-1H-pyrazolo[3,4-b]pyrazine-5-carboxamide | O=C(NCC1=CC=CN=C1)C2=NC3=C(NN=C3C4=CC=CC=C4)N=C2 | 2.24E−05 | 1.22E−07 |
| JS8 | 2-(benzo[d][1,3]dioxol-5-yl)-1-(2-(benzyloxy)phenyl)-2-methyl-6,7-dihydropyrazolo[1,5-a]pyrimidin-4(5H)-yl)ethan-1-one | CC1=NN2CCCN(C(=O)CC3=CC=CC=C40COC4=C3)C2=C1C5=CC=CC=C5OCC6=CC=CC=C6 | 8.91E−06 | 3.36E−07 |
| JS9 | 1-(3-(2-(benzyloxy)phenyl)-2-methyl-6,7-dihydropyrazolo[1,5-a]pyrimidin-4(5H)-yl)-2-(pyridin-2-yl)ethan-1-one | CC1=NN2CCCN(C(=O)CC3=CC=CC=N3)C2=C1C4=CC=CC=C4OCC5=CC=CC=C5 | 8.91E−06 | 2.17E−06 |

TABLE 1-continued

| Abr name | IUPAC name | SMILES | IC$_{50}$ GloSensor™ assay (M) | IC$_{50}$ biochem assay (M) |
|---|---|---|---|---|
| JS10 | 2-(benzo[d][1,3]dioxol-5-yl)-1-(2-methyl-3-(2-phenoxyphenyl)-6,7-dihydropyrazolo[1,5-a]pyrimidin-4(5H)-yl)ethan-1-one | CC1=NN2CCCN(C(=O)CC3=CC=C4OCOC4=C3)C2=C1C5=CC=CC=C5OC6=CC=CC=C6 | 7.94E−06 | 7.44E−07 |
| JS11 | 1-cyclohexyl-3-(cyclopropylmethyl)-N-((3-methylisoxazol-5-yl)methyl)-2-oxo-2,3-dihydro-1H-benzo[d]imidazole-5-carboxamide | CC1=NOC(CNC(=O)C2=CC=CC=C3N(C4CCCCC4)C(=O)N(CC5CC5)C3=C2)=C1 | 5.62E−06 | 1.14E−06 |
| JS12 | (1-(4-methoxyphenyl)cyclopropyl)(5-methyl-5,6-dihydrospiro[benzo[f]imidazo[1,2-a][1,4]diazepine-4,4'-piperidin]-1'-yl)methanone | COC1=CC=C(C(=C1)C2(CC2)C(=O)N3CCCC4(CC3)N(C)C5=CC=CC=C5)N6C=CN=C46 | 8.91E−06 | 6.14E−07 |
| JS13 | N-benzyl-1-(2-cyanobenzyl)-4-oxo-1,5-diazacycloundecane-8-carboxamide | O=C(NCC1=CC=CC=C1)C2CCCN(CC3=C(C=CC=C3)C#N)CCCC(=O)NCC2 | 3.98E−06 | 1.19E−06 |
| JS14 | N-benzyl-N-methyl-8-phenylimidazo[1,2-a]pyrazine-2-carboxamide | C1(N=C(N(C=1)C=C1)C(=N1)C(=CC1)C=CC=1)CN(CC(=CC1)C=CC=1)C)=O | 6.31E−06 | 1.86E−05 |

Data Analysis

GraphPad Prism™ 7.0 (GraphPad) was used to fit concentration-response curves and calculate $IC_{50}$ and $I_{max}$ values. Differences between mean values were analyzed using two-tailed Student's t-test (two groups) or one-way analysis of variances (ANOVA) with Tukey's post-hoc test (more than two groups). Differences were considered significant for $p<0.05*$, $p<0.01$, and $p<0.001*$.

The counter-screens that were performed to eliminate false positives from among the candidate inhibitors led to the identification of a small group of about 20 hNpr1 antagonists, of which fifteen are described in the tables herein. These fifteen compounds also inhibited hNpr2 but had no direct effect on Firefly luciferase, were not cytotoxic, and did not interfere with SNP-induced GloSensor™ signals. The fifteen most efficacious hNpr1 inhibitors from the GloSensor™ assays were selected for the validation assay and inhibitory effects were corroborated for each compound. In particular, the apparent potency ($IC_{50}$) and efficacy ($I_{max}$) in five different assays for each candidate compound was tabulated: Inhibition of hNppa-stimulated HEK-hNpr1-cGMP-sensor cells, inhibition of Nppc-stimulated HEK-hNpr2-cGMP-sensor cells, inhibition of SNP-stimulated HEK-cGMP-sensor cells, inhibition of Firefly luciferase in vitro, and cytotoxicity on HEK-hNpr1-cGMP-sensor cells. Concentration-response-curve in each assay was fit with a four-parameter logistic regression. For counter-screens, potency and efficacy of compounds frequently could not be determined as fits did not converge (n. c.) and inhibition was not detectable at all (n. d.), respectively. For each compound, potency (as the $IC_{50}$ in μM) and efficacy (as $I_{max}$ in %), are given in Table 2.

TABLE 2 qHTS and Various Counter-screens Reveal bona-fide hNpr1 Inhibitors.

| Compound | HEK-hNpr1-cGMP-sensor cells | | HEK-hNpr2-cGMP-sensor cells | | HEK-cGMP-sensor cells | | Fluc in vitro | | cytotoxicity | |
|---|---|---|---|---|---|---|---|---|---|---|
| | $IC_{50}$ | $I_{max}$ | $IC_{50}$ | $I_{max}$ | $IC_{50}$ | $I_{max}$ | $IC_{50}$ | $I_{max}$ | $IC_{50}$ | $I_{max}$ |
| JS-1 | 26 ± 1.5 | −119 ± 20 | 7.2 ± 1.3 | −106 ± 8 | n.c. | n.d. | 0.03 ± 1.5 | −3 ± 3 | n.c. | n.d. |
| JS-2 | 25 ± 1.3 | −102 ± 9 | 6.4 ± 1.1 | −88 ± 5 | n.c. | n.d. | n.c. | n.d. | n.c. | n.d. |
| JS-3 | 62 ± 19 | −183 ± 67 | 17 ± 20 | −126 ± 23 | n.c. | n.d. | 25 ± 4 | −1 ± 6 | n.c. | n.d. |
| JS-4 | 16 ± 13 | −110 ± 10 | 11 ± 1.2 | −100 ± 5 | n.c. | n.d. | n.c. | n.d. | n.c. | n.d. |
| JS-5 | 32 ± 13 | −127 ± 12 | 12 ± 1.1 | −97 ± 4 | n.c. | n.d. | n.c. | n.d. | n.c. | n.d. |
| JS-6 | 24 ± 1.2 | −15 ± 3 | 6.9 ± 1.1 | −102 ± 3 | n.c. | n.d. | n.c. | n.d. | 45 ± 43 | −36 ± 87 |
| JS-7 | 85 ± 22 | −216 ± 97 | 16 ± 1.3 | −122 ± 11 | n.c. | n.d. | n.c. | n.d. | n.c. | n.d. |
| JS-8 | 13 ± 1.2 | −122 ± 9 | 9.1 ± 1.4 | −127 ± 13 | n.c. | n.d. | n.c. | n.d. | 49 ± 14 | −22 ± 29 |
| JS-9 | 35 ± 15 | −106 ± 18 | 20 ± 16 | −102 ± 16 | n.c. | n.d. | n.c. | n.d. | n.c. | n.d. |
| JS-10 | 17 ± 1.3 | −122 ± 12 | 5.4 ± 1.4 | −86 ± 5 | n.c. | n.d. | n.c. | n.d. | n.c. | n.d. |
| JS-11 | 21 ± 1.3 | −140 ± 13 | 5.0 ± 1.1 | −97 ± 4 | n.c. | n.d. | n.c. | n.d. | n.c. | n.d. |
| JS-12 | 16 ± 1.3 | −116 ± 11 | 5.7 ± 1.1 | −96 ± 4 | n.c. | n.d. | n.c. | n.d. | n.c. | n.d. |
| JS-13 | 10 ± 1.2 | −99 ± 6 | 5.9 ± 1.3 | −108 ± 8 | n.c. | n.d. | n.c. | n.d. | n.c. | n.d. |
| JS-14 | 117 ± 75 | −286 ± 966 | 20 ± 1.1 | −91 ± 8 | n.c. | n.d. | n.c. | n.d. | n.c. | n.d. |
| JS-15 | 6.9 ± 2.0 | −41 ± 8 | 41 ± 13.8 | −41 ± 8 | n.c. | n.d. | n.c. | n.d. | n.c. | n.c. |

Additional screens of the fifteen candidates corroborated hNpr1 inhibition. In particular, HEK-hNpr1-cGMP-sensor cells were seeded in 96-wells and stimulated with 60 pM hNppa 5 minutes after addition of candidate compounds or A-71915 and luminescence was measured for 30 minutes. Inhibitors were titrated to calculate apparent potency ($IC_{50}$) and efficacy ($I_{max}$) of inhibition of hNppa-induced cGMP production. The results are set forth in Table 3.

TABLE 3

Detailed Analysis of Candidate Compounds in GloSensor™ assay, Conducted in 96-well Format, Corroborates hNpr1 Inhibition.

| Compound | $IC_{50}$ [μM] (mean ± SEM) | $I_{max}$ [%] (mean ± SEM) |
|---|---|---|
| JS-3 | 3.1 ± 0.6 | −99.4 ± 0.6 |
| JS-4 | 1.1 ± 0.01 | −95.5 ± 1.2 |
| JS-5 | 7.4 ± 0.3 | −99.9 ± 0.1 |
| JS-6 | 1.9 ± 0.1 | −94.2 ± 5.3 |
| JS-7 | 1.2 ± 0.5 | not determined |
| JS-8 | 1.2 ± 0.1 | −98.8 ± 0.7 |
| JS-9 | 3.1 ± 1.4 | −93.4 ± 6.4 |
| JS-10 | 6.7 ± 6.7 | −98.3 ± 1.7 |
| JS-11 | 1.9 ± 0.8 | −96.3 ± 1.3 |
| JS-12 | 1.3 ± 0.002 | −96.0 ± 1.3 |
| JS-13 | 1.1 ± 0.1 | −96.1 ± 0.4 |
| JS-14 | 3.1 ± 1.1 | not determined |
| A-71915 | 1.1 ± 0.1 | −99.8 ± 0.1 |

It was determined that three candidates, JS-5, JS-8, and JS-11, inhibit hNpr1 activity, but do not attenuate SNP dependent cGMP sensor activation, do not directly inhibit luciferase, and are not cytotoxic (FIGS. 3A-3F). However, these compounds also inhibited hNpr2 with similar potency to hNpr1 (FIGS. 8A-C), suggesting that the inhibitors identified do not distinguish between hNpr1 and hNpr2. The structures of JS-5, JS-8, and JS-11 are similar to each other (FIGS. 3B, 3D, and 3F), suggesting a common mode of action and a potential common binding site.

Example 2

This example demonstrates that A-71915 is a partial agonist of Npr1.

It has been reported that the Npr1 antagonist A-71915 does not block acute itch responses elicited by the intradermal injection of pruritogens in mice, but the reason has been heretofore unexplained. One potential explanation for why A-71915 does not effectively block itch in vivo is that it may be a poor inhibitor. To investigate this possibility, a method to measure inhibition of mouse Npr1 (mNpr1) by A-71915 was developed, discussed below.

Figure 1A:
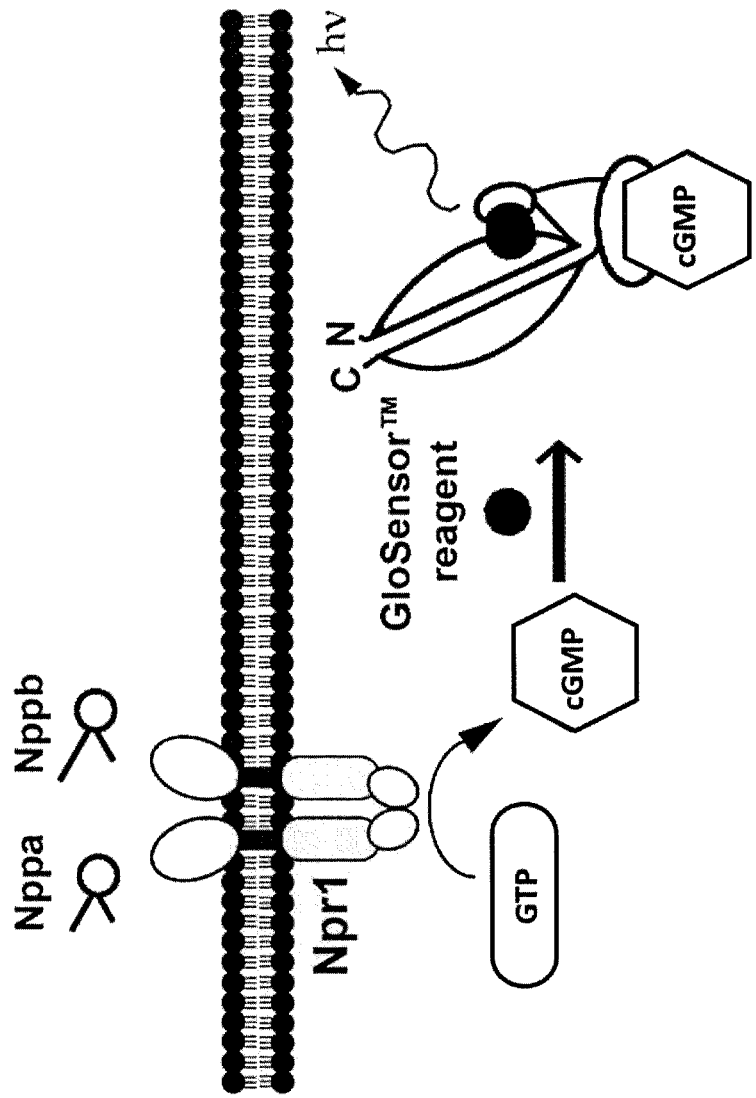
Figure 1B:
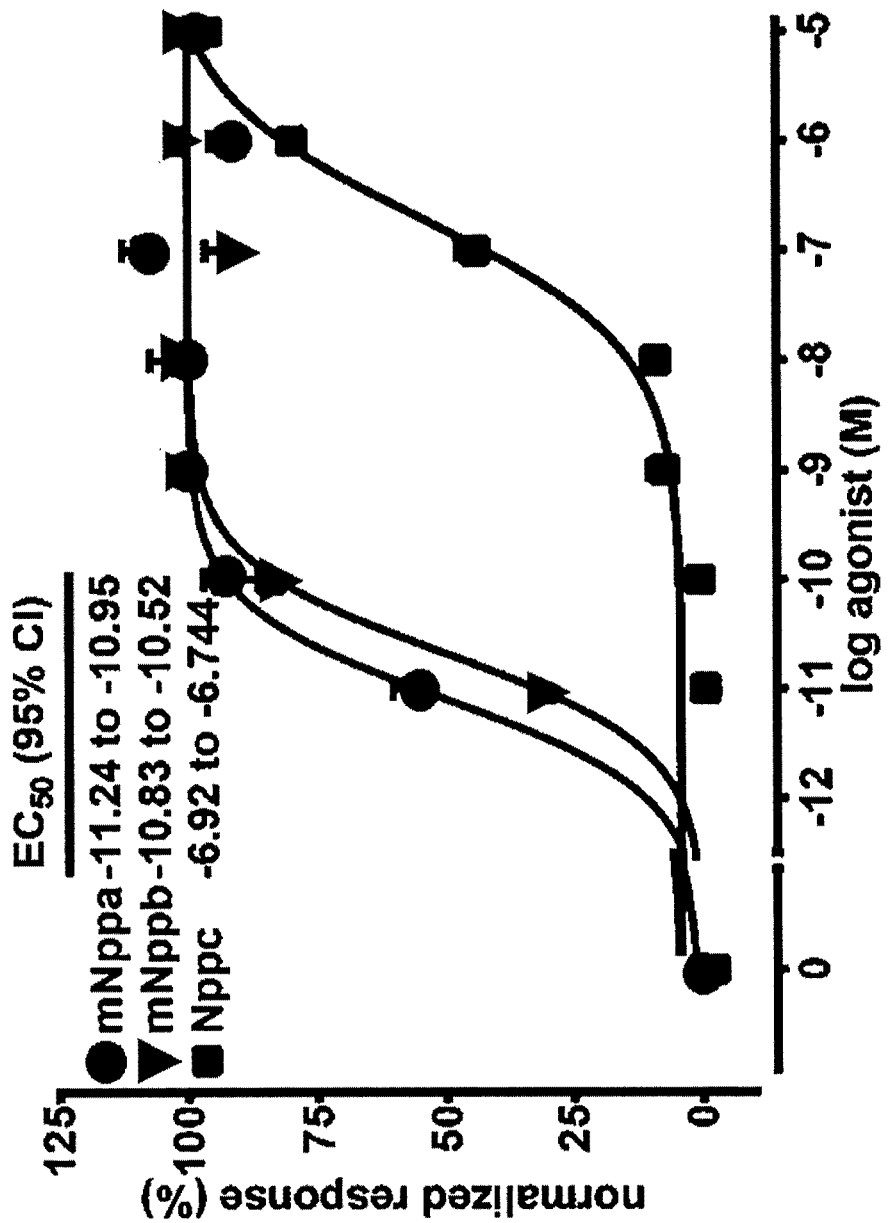
Figure 1C:
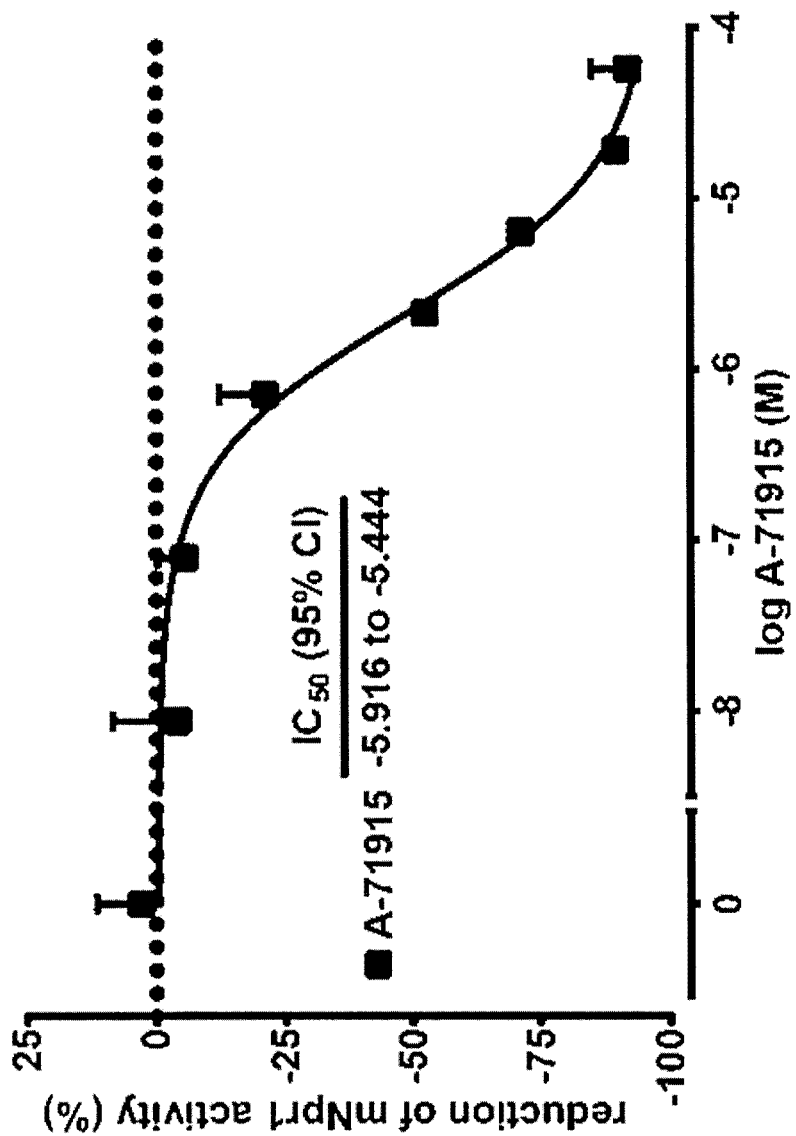
Figure 1D:
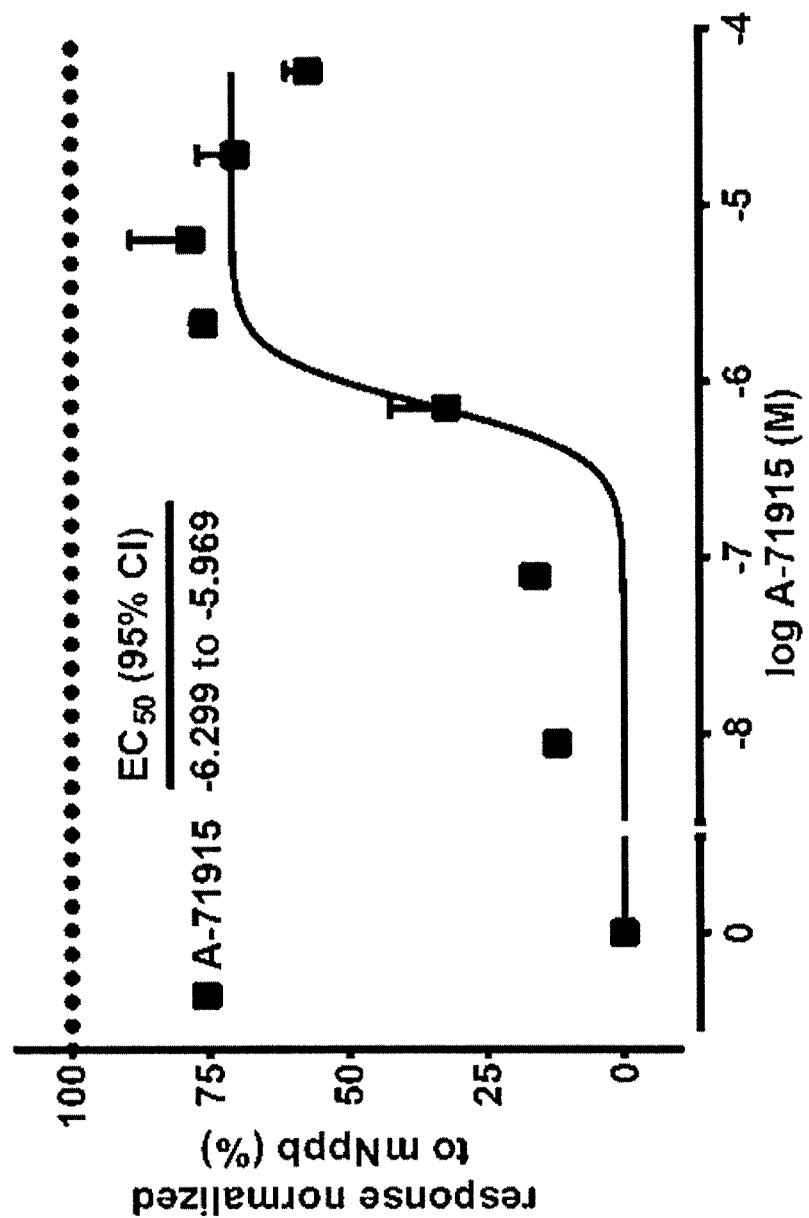
Figure 1E:
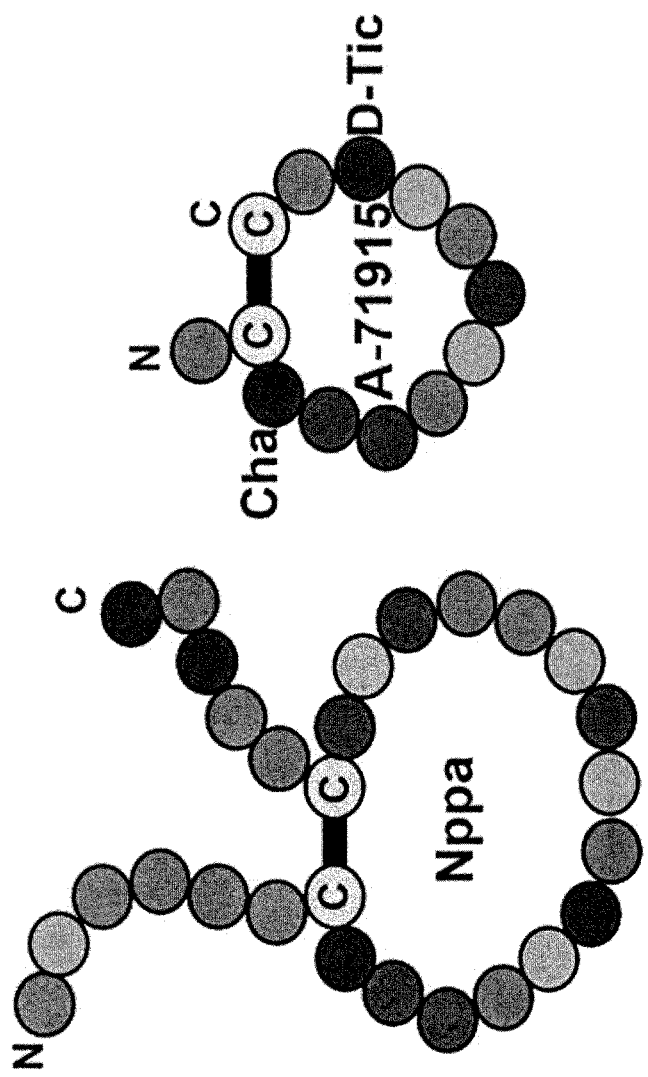
Figure 2A:
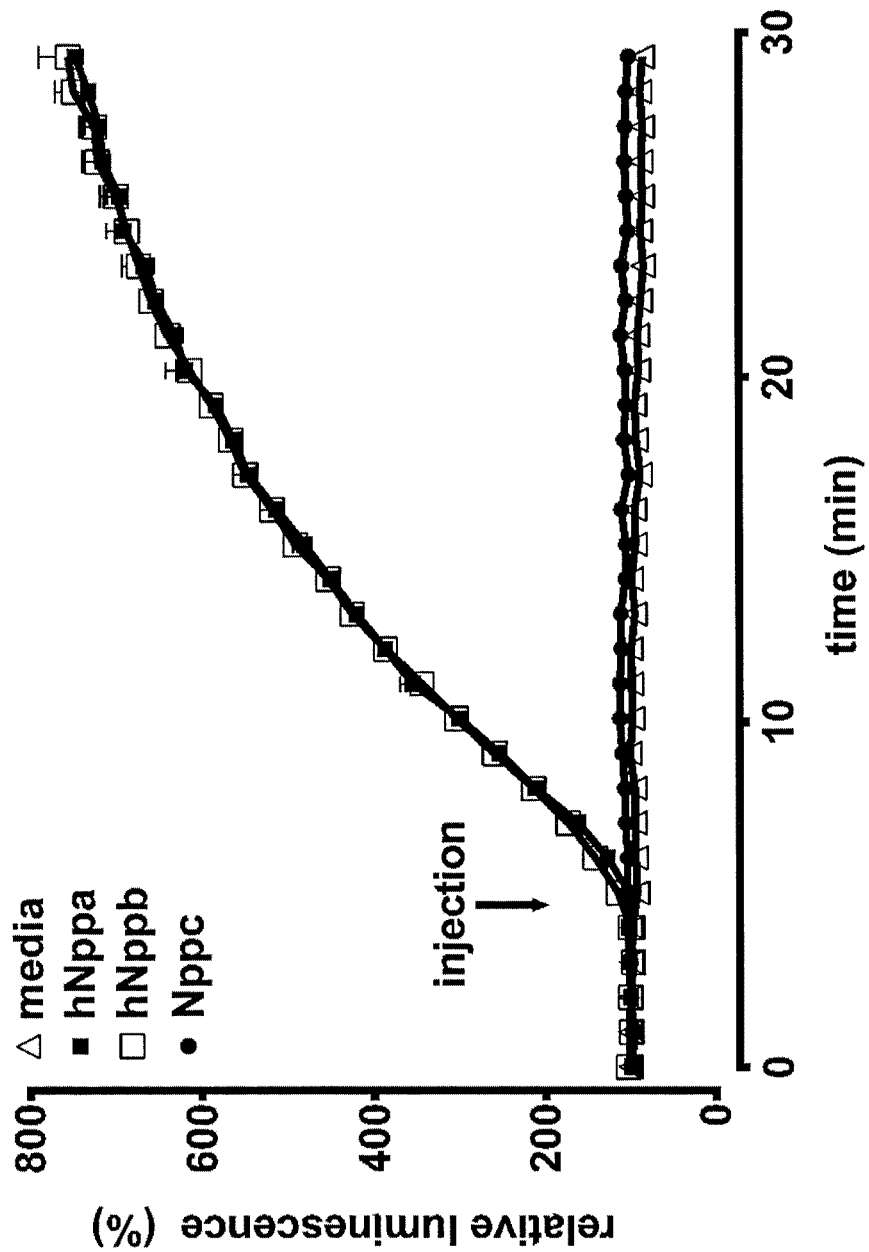
Figure 2B:
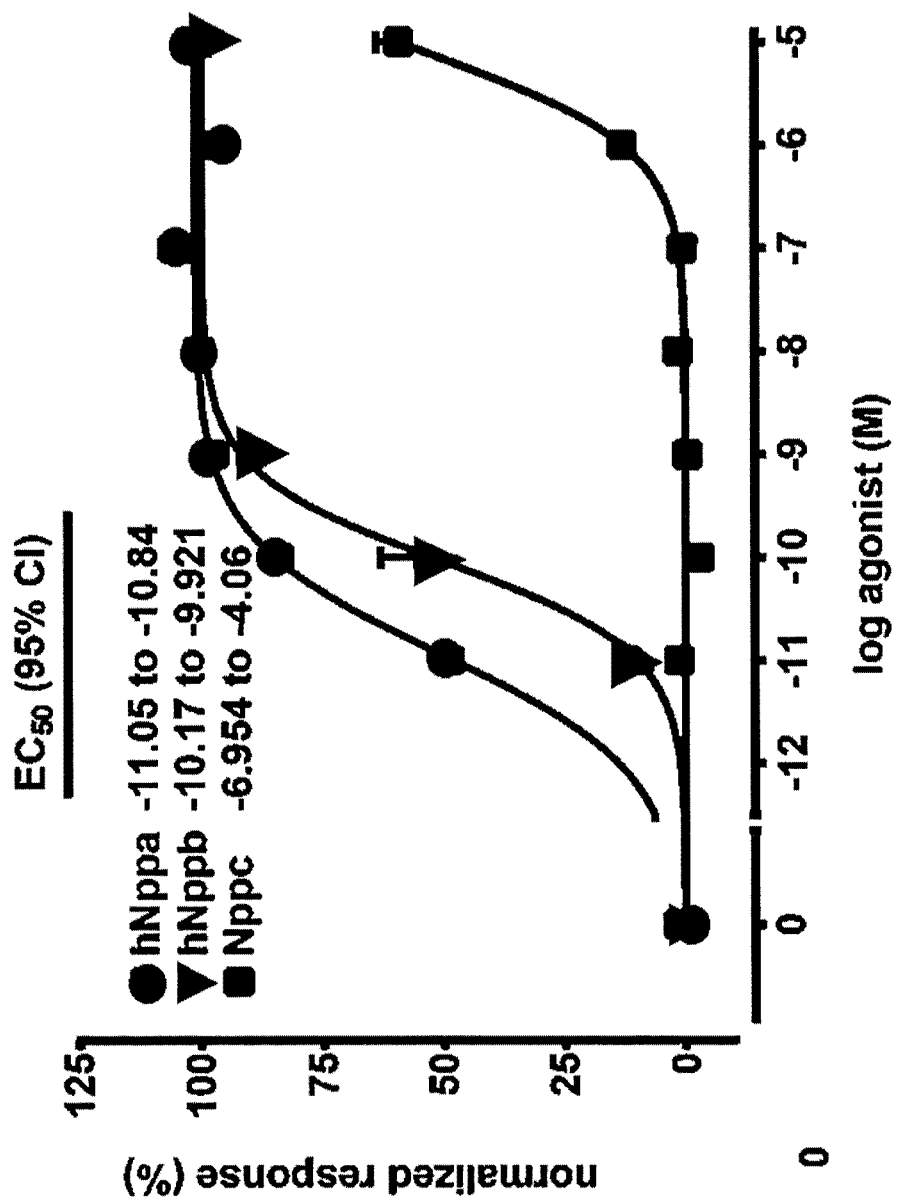
Figure 2C:
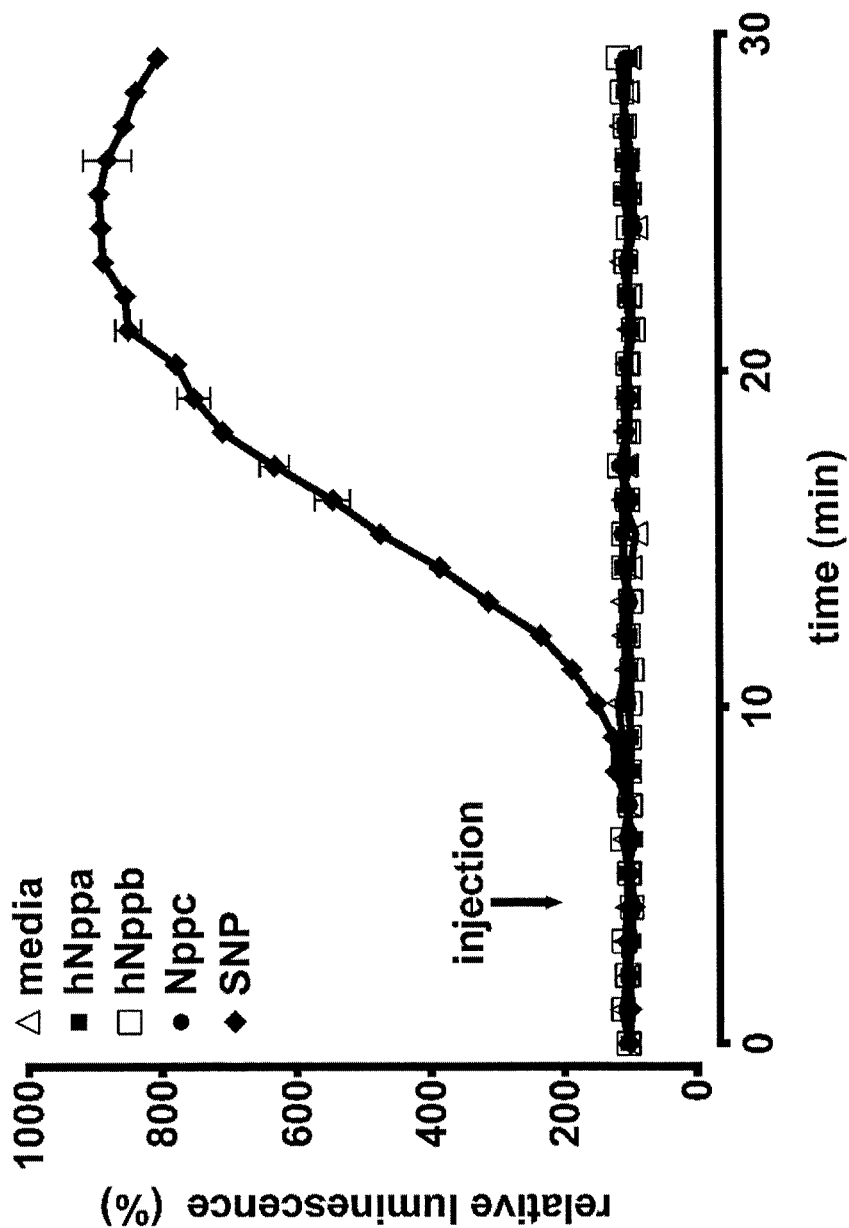
Figure 2D:
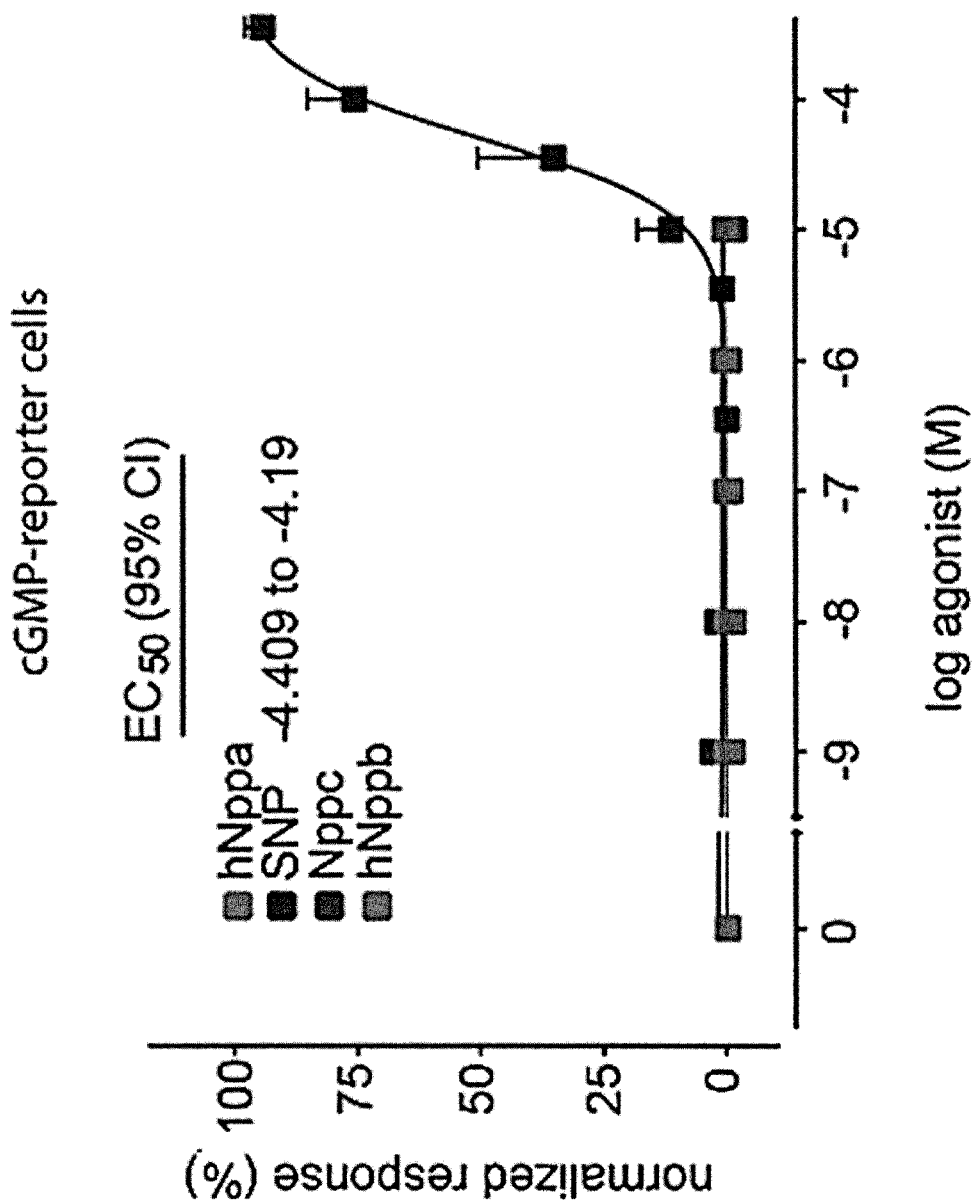
Figure 2E:
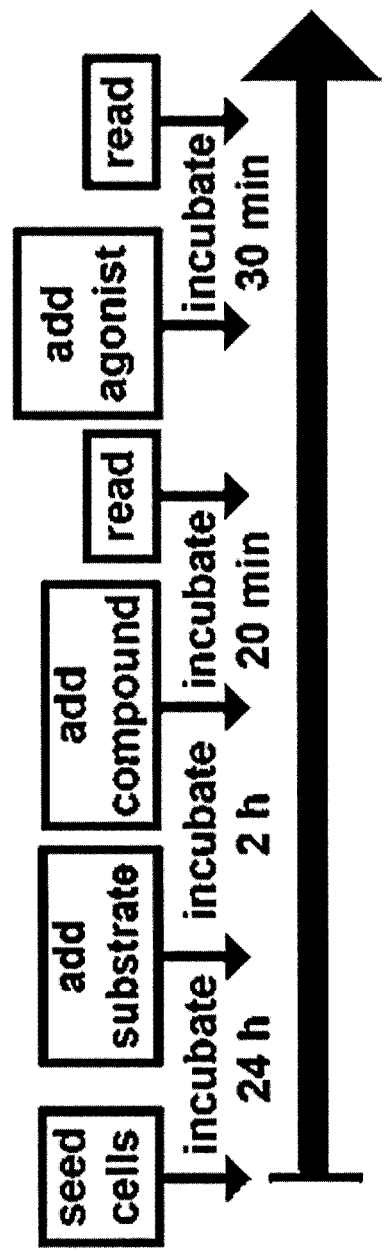
Figure 2F:
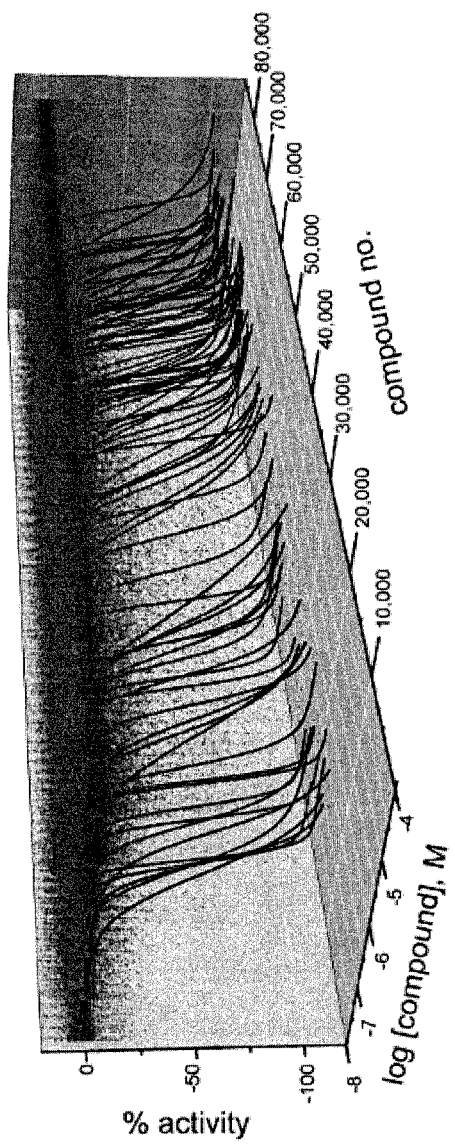
Figure 3B:
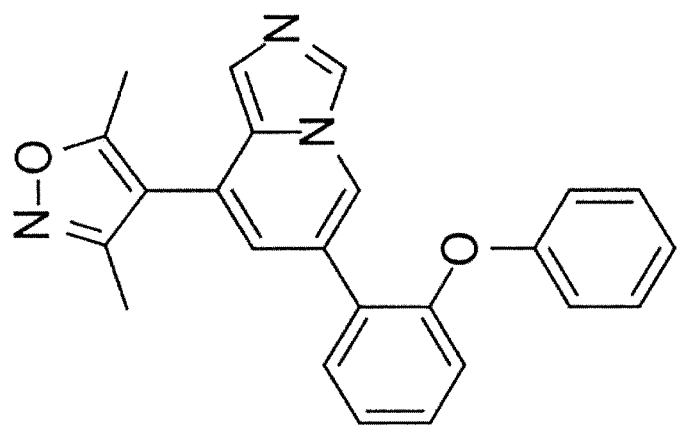
FIG. 3B is a schematic diagram of the chemical structure of JS-5.
Figure 3A:
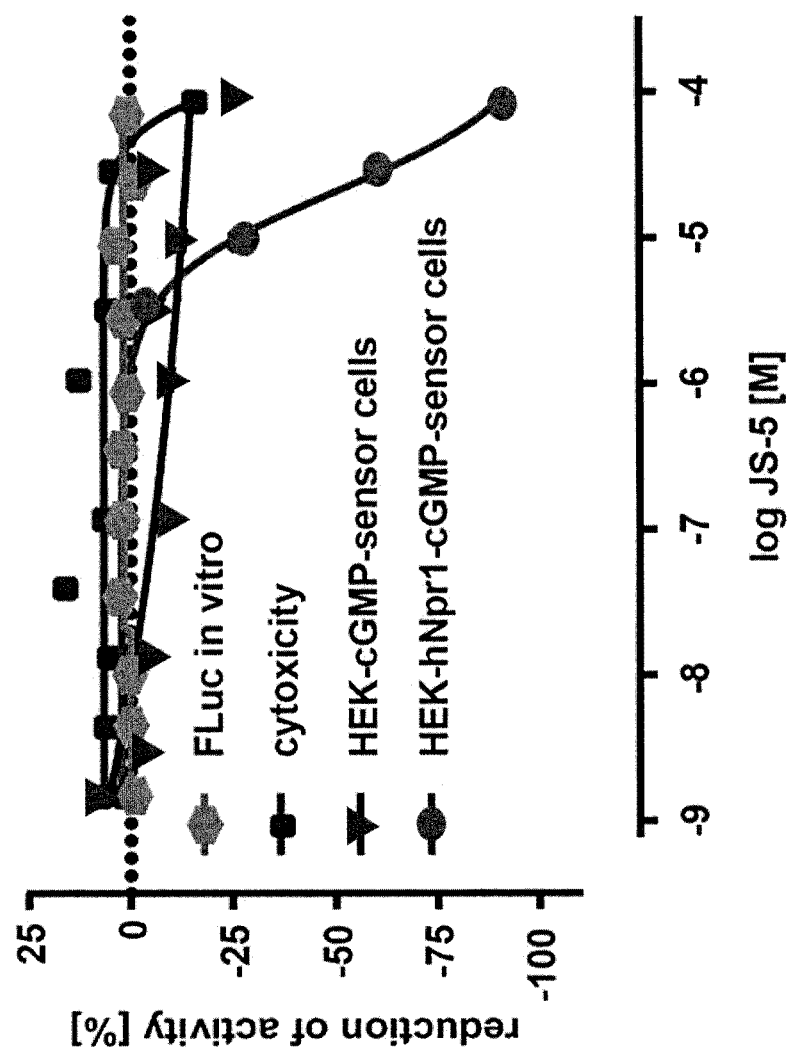
FIG. 3A is a graph showing that compound JS-5 inhibits hNppa-induced hNpr1 activity in HEK-hNpr1-cGMP-sensor cells, does not inhibit Firefly luciferase (FLuc in vitro), does not block SNP-induced GloSensor™ signals (in HEK-cGMP-sensor cells), and does not produce cytotoxicity. Data are measurements from the qHTS assays.
Figure 3F:
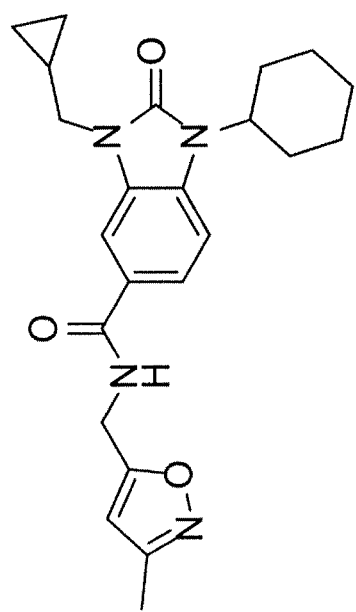
FIG. 3F is a schematic diagram of the chemical structure of JS-11.
Figure 3E:
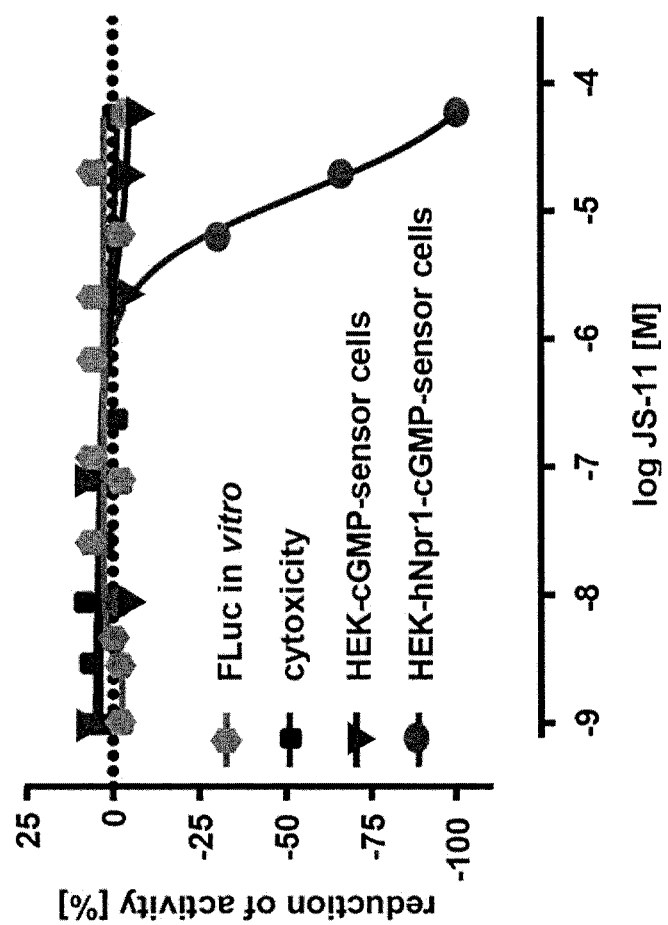
FIG. 3E is a graph showing that compound JS-11 inhibits hNppa-induced hNpr1 activity in HEK-hNpr1-cGMP-sensor cells, does not inhibit Firefly luciferase (FLuc in vitro), does not block SNP-induced GloSensor™ signals (in HEK-cGMP-sensor cells), and does not produce cytotoxicity. Data are measurements from the qHTS assays.

Because the Npr1 receptor is a ligand-dependent guanylate cyclase, measuring agonist-induced changes in intracellular cGMP levels was used to examine inhibition of Npr1. To measure the production of cGMP by Npr1, a circular permutated Firefly luciferase molecule which was functionally linked to the cGMP binding domain of human PDE5 (GloSensor™ technology pGS-40F) was used, as described in Example 1. This reporter molecule together with a luciferase substrate (GoSensor™ reagent) and a sensitive method for detection of luciferase activity (emitted light) permitted real-time measurement of cGMP levels in live cells (FIG. 1A). The cGMP sensor was expressed in HEK293 cells and luciferase activity after stimulation with the NO-donor sodium nitroprusside (SNP), which activates ubiquitously expressed soluble guanylate cyclases, was examined. It was found that SNP generated a dose dependent increase in luciferase activity. In contrast, stimulation of these cGMP reporter cells with natriuretic peptides did not increase cGMP, indicating that HEK293 cells do not express detectable endogenous natriuretic peptide receptors. Next, mNpr1 and the cGMP sensor were transiently expressed in HEK293 cells and agonist dependent receptor activation was examined. It was found that natriuretic peptides dose dependently increased reporter activity and had stimulation potencies similar to those previously reported (FIG. 1B). Next, the effects of A-71915 on mNpr1 were tested. It was found that A-71915 blocks agonist-induced mNpr1 activity with an $IC_{50}$ of 2 µM (FIG. 1C). In the absence of natriuretic peptides, A-71915 evoked a dose-dependent activation of mNpr1, indicating that, instead of being a neutral antagonist, A-71915 acts as a partial agonist (FIG. 1D). It was hypothesized that because A-71915 is highly structurally related to natriuretic peptides, as shown in FIG. 1E, it likely competes with natriuretic polypeptides for the same binding site. The fact that A-71915 is a partial agonist, not a full neutral antagonist, provides a potential explanation for the lack of efficacy of A-71915 in blocking itch behavior.

This example demonstrates that A-71915 can be used as a comparative compound to the candidate Npr1 antagonist compounds provided herein, according to embodiments of the invention.

Example 3

This example demonstrates the validation of the candidate hNpr1 inhibitors identified according to an embodiment of the invention.

Twelve compounds were selected from those identified in Table 1 which could be obtained in large amounts at high purity (JS-3 through JS-14). Next, an independent strategy was developed to confirm the direct inhibition of hNpr1 by these compounds (FIG. 4A). The approach used was to directly determine cGMP production by stimulated hNpr1 using an in vitro cyclase assay with subsequent measurement of cGMP using ELISA. The cGMP cyclase activity of membranes isolated from HEK293-hNpr1-cGMP sensor cells was measured. It was found that the activation of hNpr1 with hNppa increased cGMP levels, while activation of membranes with SNP did not (FIG. 4B). All novel hNpr1 inhibitors could completely block cGMP production by hNpr1, as shown in FIG. 4C and Table 4. In particular, membrane fractions were prepared from HEK-hNpr1-cGMP-sensor cells and in vitro cyclase assays were conducted to determine hNpr1 inhibition by the given compounds as described in Example 1. The inhibitory effects of Npr1 antagonists were quantified and the potency of this response was calculated by fitting the data to a four-parameter logistic curve. The results are set forth in Table 4.

TABLE 4

Cell-free Npr1 Membrane Cyclase Assay Confirmed That Candidate Compounds Are Specific hNpr1 Antagonists.

| Compound | $IC_{50}$ [µM] (mean ± SEM) | $I_{max}$ [%] (mean ± SEM) |
|---|---|---|
| JS-3 | 4.0 ± 1.2 | −98.2 ± 1.8 |
| JS-4 | 2.8 ± 0.04 | −96.1 ± 3.7 |
| JS-5 | 0.1 ± 0.1 | −99.8 ± 0.1 |
| JS-6 | 0.8 ± 1.9 | −99.4 ± 0.5 |
| JS-7 | 0.1 ± 0.3 | −98.4 ± 1.5 |
| JS-8 | 0.3 ± 0.4 | −98.0 ± 2.0 |
| JS-9 | 2.2 ± 1.8 | −95.3 ± 4.5 |
| JS-10 | 0.7 ± 0.6 | −95.2 ± 3.3 |
| JS-11 | 1.4 ± 0.1 | −99.7 ± 0.2 |
| JS-12 | 0.7 ± 0.1 | −99.0 ± 1.0 |
| JS-13 | 0.8 ± 0.9 | −94.4 ± 5.4 |
| JS-14 | 12.7 ± 4.9 | −99.0 ± 0.0 |
| A-71915 | 0.1 ± 0.03 | −98.0 ± 3.5 |

As noted, the reduction in hNpr1 activity of compounds JS-5, JS-8, and JS-11 is also shown in FIG. 4C. The recorded potencies of inhibitory compounds on hNpr1 in the in vitro and cell-based assays, when corrected for differences in assay sensitivity, were very similar (Tables 5 and 6). In particular, data from tables 3, 4, and 6 (below) were used to calculate the inhibitor constant $K_i$ for novel Npr1 antagonists, using the Cheng-Prusoff equation $$K_i = \frac{IC_{50}}{1 + \frac{[Npp]}{EC_{50}}}.$$

This calculation corrects for differences in assay sensitivity thereby allowing the comparison of hNpr1 inhibition across different functional assays or the comparison of inhibition of Npr1 from different species.

TABLE 5

Calculated $K_i$ Values for hNpr1 and mNpr1 Are Similar Among Both Receptors and Different Assays.

| Compound | $K_i$ hNpr1 GloSensor™ [µM] (mean ± SEM) | $K_i$ hNpr1 cyclase assay [µM] (mean ± SEM) | $K_i$ mNpr1 GloSensor™ [µM] (mean ± SEM) |
|---|---|---|---|
| JS-3 | 0.50 ± 0.102 | 0.58 ± 0.179 | 0.25 ± 0.036 |
| JS-4 | 0.18 ± 0.002 | 0.41 ± 0.006 | 0.22 ± 0.070 |
| JS-5 | 1.18 ± 0.048 | 0.02 ± 0.020 | 0.42 ± 0.265 |
| JS-6 | 0.31 ± 0.023 | 0.11 ± 0.275 | 1.69 ± 1.395 |
| JS-7 | 0.19 ± 0.085 | 0.02 ± 0.044 | not determined |
| JS-8 | 0.20 ± 0.013 | 0.05 ± 0.064 | 0.10 ± 0.006 |
| JS-9 | 0.49 ± 0.215 | 0.32 ± 0.262 | 0.57 ± 0.0004 |
| JS-10 | 1.07 ± 1.079 | 0.11 ± 0.090 | 0.31 ± 0.037 |
| JS-11 | 0.30 ± 0.134 | 0.21 ± 0.008 | 0.10 ± 0.030 |
| JS-12 | 0.21 ± 0.0002 | 0.10 ± 0.015 | 0.26 ± 0.006 |
| JS-13 | 0.18 ± 0.011 | 0.12 ± 0.130 | 0.21 ± 0.046 |
| JS-14 | 0.50 ± 0.179 | 1.87 ± 0.723 | 0.32 ± 0.329 |
| A-71915 | 0.18 ± 0.016 | 0.02 ± 0.004 | 0.05 ± 0.005 |

For Table 6, HEK-293 cells transiently expressing mNpr1 and pGS-40F were stimulated with 1 nM mNppb 5 minutes after addition of candidate compounds or A-71915 and luminescence was measured for 30 minutes. Inhibitors were titrated to calculate apparent $IC_{50}$ values, as described in methods.

TABLE 6

Novel hNpr1 Inhibitors also Inhibit mNpr1.

| Compound | IC$_{50}$ [µM] (mean ± SEM) |
|---|---|
| JS-3 | 12 ± 1.8 |
| JS-4 | 11 ± 3.4 |
| JS-5 | 20 ± 12 |
| JS-6 | 82 ± 68 |
| JS-7 | n.d. |
| JS-8 | 4.7 ± 0.3 |
| JS-9 | 28 ± 0.02 |
| JS-10 | 15 ± 1.8 |
| JS-11 | 4.9 ± 1.5 |
| JS-12 | 13 ± 0.3 |
| JS-13 | 10 ± 2.2 |
| JS-14 | 15.8 ± 16 |
| A-71915 | 2.2 ± 0.3 |

During the screening, it was found that both the basal and agonist-induced hNpr1 activity were inhibited by the JS-5, JS-8, and JS-11 inhibitors (FIG. 5A). Because A-71915 behaves like a weak partial agonist, it was hypothesized that the compounds identified might inhibit hNpr1 via a different mechanism from A-71915. To explore this further, hNppa was titrated against fixed concentrations of A-71915 and the three antagonists JS-5, JS-8, JS-11 (FIGS. 5B-C). While A-71915 induced aright-shift in hNppA potency without any effect on maximal efficacy, JS-5, JS-8, and JS-111 reduced maximal responses even at extremely high hNppa concentrations (10$^5$-fold higher than EC$_{50}$). This lack of effect of increased agonist concentrations could either indicate anoncompetitive inhibition of hNpr1 or could be explained by the slow dissociation of the antagonists from hNpr1. If the latter were true, it would be expected that washing Npr1 expressing cells after incubation with antagonist would have little effect on receptor inhibition. To examine this possibility, the HEK-hNpr1-cGMP-sensor cells were treated with JS-8 for 5 minutes and, after a 5-minute washing step, cells were stimulated with 60 µM hNppa. Inhibition of hNppa-induced hNpr1 activation after washing was compared to the control condition (ctrl; cells acutely pre-treated with JS-8 for 5 minutes and immediately stimulated with 60 µM hNppa). It was found that even a single washing step was sufficient to completely recover hNpr1 activity (FIG. 5D), suggesting that the antagonists identified do not have slow dissociation, but likely block hNpr1 via a reversible non-competitive mechanism.

Example 4

This example demonstrates the inhibition of itch in mouse models by the Npr1 antagonist compounds identified according to an embodiment of the invention. To determine whether the identified inhibitors of Npr1 could alleviate itch, the inhibitory effect of the identified compounds (JS-3 through JS-14) on mNpr1 was examined. Comparison of inhibition efficacy on hNpr1 and mNpr1 revealed, when corrected for differences in assay sensitivity, that most of the identified compounds had similar potencies (Tables 5 and 6), suggesting they might block itch in vivo in a mouse model of itch.

As a proof-of-concept, the ability of one of the identified compounds to inhibit itch responses was investigated. Compound JS-11 was chosen because of its relatively high-water solubility, high membrane permeability (7.4×10$^{-6}$ cm/sec), and moderate half-life (12.4 min). The behavioral measurements of mouse scratching behavior were assessed as follows.

Behavioral Measurement of Acute Scratching Behavior

All experiments using mice followed NIH guidelines and were approved by the National Institute of Dental and Craniofacial Research ACUC. Behavioral assessment of scratching behavior was conducted as follows: 6-8-week old female C57BL/6N mice (Envigo) were injected intraperitoneally with JS-11 (163 µg) or DMSO (20%) as a vehicle control. Ten minutes later, 100 µg histamine diluted in 10 µl PBS or 8.9 µg CYM5442 diluted in 10 µl ddH$_2$O was injected subcutaneously into the nape of the neck. Scratching behavior was recorded for 30 minutes and is presented in bouts per 30 minutes. One bout was defined as scratching behavior towards the injection site between lifting the hind leg from the ground and either putting it back on the ground or guarding the paw with the mouth. To control for motor impairment by JS-11, rota-rod performance was also assessed 10 minutes after intraperitoneal injection.

Behavioral Measurement of Chronic Scratching Behavior

The contact hypersensitivity model was performed as follows: the back of 6-8-week old female C57BL/6N mice (Envigo) was shaved with electric clippers. After 2 days, 25 µl of 0.5% (v/v) dinitro-fluoro-benzene (DNFB) diluted in a 4:1 mixture of acetone and olive oil was applied to the shaved back skin. Hapten challenge was performed 5 days after sensitization by applying 40 µl of 0.2% (v/v) DNFB in the same vehicle on the left ear and 40 µl of vehicle alone on the right ear. After 24 hours, baseline scratching was observed for 30 minutes. Mice were then injected intraperitoneally with JS-11 (163 µg) or DMSO (20%) as a vehicle control. After 10 minutes, scratching was again observed for 30 minutes. To assess skin inflammation, ear thickness was measured with a thickness gauge (Mitutoyo, Aurora, Ill.) before and 30 minutes after JS-11/DMSO injections and normalized to ear thickness before hapten challenge. Hapten challenge (left ear) induced significantly more skin inflammation than application of vehicle alone (right ear).

Intraperitoneal injection of 163 µg JS-11 produced no gross change in overall mouse behavior and rotarod measurements showed that JS-11 induced no impairment of motor coordination ten minutes after JS-11 treatment (FIG. 6A). Next, whether scratching responses were attenuated by JS-11 was tested, as described in Example 5. Scratching responses to pruritogens injected intradermally into the nape of the neck (100 µg histamine and 8.9 µg CYM5442) were significantly attenuated compared to paired controls by administration of JS-11. JS-11 reduced scratching responses to histamine by more than half (FIG. 6B). To corroborate this result, the pruritogen CYM5442 which activates the sphingosine-1-phosphate receptor 1, was tested in sensory neurons. Pairwise comparison showed that JS-11 strongly attenuated itch response (FIG. 6C). Significant differences were assessed by using paired Student's t-test (histamine: p=0.0221, and CYM5442: p=0.0128). Data represent means±SEM of n=10 (FIGS. 6A and 6C) and 8 animals (FIG. 6B).

Next, to investigate whether Nppb is co-expressed with known itch receptors, double labelling ISH (in situ hybridization) on human DRG (dorsal root ganglion) sections with Nppb and the histamine receptor HRH1, and MRGPRX1, a receptor of the pruritic bovine adrenal medulla peptide 8-22 and the anti-malaria drug chloroquine was performed. It was found that HRH1 is exclusively co-expressed with Nppb (FIG. 6D; 106 out of 107 DRG neurons) and that all MRGPRX1-positive cells co-express Nppb, although some Nppb expressing cells were MRGPRX1 negative (FIG. 6E; 121 of 150 NPPB$^+$ DRG neurons express MRGPRX1).

Next, whether Nppb is expressed with the receptor for interleukin-31 (IL-31), IL-31 receptor A (IL31RA) was investigated. As with HRH1 and MRGPRX1 itch receptors, ISH revealed that human DRG neurons expressing Nppb co-express IL31RA (FIG. 9A; 119 of 126 DRG neurons). To further investigate the significance of this co-expression in vivo, the potential for blocking IL31-mediated itch with Npr1 antagonist in a mouse model of contact hypersensitivity was investigated (FIG. 8B). In this model, scratching but not skin inflammation is dependent on IL-31. As assessed by measuring ear thickness after hapten challenge, acute blockade with JS-11 had no effect on skin inflammation (FIG. 9C). By contrast, JS-11 attenuated hapten-induced scratching responses by about a half (FIG. 9D).

This example demonstrates that inhibition of Npr1 by JS-11, and blocking Nppb neurotransmission are viable approaches for attenuation of human itch. These results also indicate that ongoing peripheral drive contributes to pruritus in a model of persistent inflammatory dermatitis and suggests that clinically, blocking Npr1 might be a valuable approach to treat patients with chronic itch.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising (a) a pharmaceutically acceptable carrier and (b) a molecular inhibitor of Natriuretic polypeptide receptor 1 ("Npr1"), wherein the molecular inhibitor of Npr1 is
  1-cyclohexyl-3-(cyclopropylmethyl)-N-((3-methylisoxazol-5-yl)methyl)-2-oxo-2,3-dihydro-1H-benzo[d]imidazole-5-carboxamide.

2. The pharmaceutical composition of claim 1, wherein the Npr1 is the human isoform of Npr1 ("hNpr1").

* * * * *